(12) United States Patent
Brunell et al.

(10) Patent No.: US 7,758,537 B1
(45) Date of Patent: Jul. 20, 2010

(54) SYSTEMS AND METHODS FOR ELECTROSURGICAL REMOVAL OF THE STRATUM CORNEUM

(75) Inventors: Stephen M. Brunell, San Ramon, CA (US); Jean Woloszko, Austin, TX (US); Michael A. Baker, Austin, TX (US); Hira V. Thapliyal, Los Altos, CA (US); Philip E. Eggers, Dublin, OH (US)

(73) Assignee: ArthroCare Corporation, Austin, TX (US)

( * ) Notice: Subject to any disclaimer, the term of this patent is extended or adjusted under 35 U.S.C. 154(b) by 183 days.

(21) Appl. No.: 09/293,231

(22) Filed: Apr. 16, 1999

Related U.S. Application Data

(63) Continuation-in-part of application No. 09/248,763, filed on Feb. 12, 1999, now Pat. No. 6,149,620, which is a continuation-in-part of application No. 08/977,845, filed on Nov. 25, 1997, now Pat. No. 6,210,402, which is a continuation-in-part of application No. 08/562,332, filed on Nov. 22, 1995, now Pat. No. 6,024,733.

(51) Int. Cl.
*A61B 17/20* (2006.01)
(52) U.S. Cl. ........................................................ 604/22
(58) Field of Classification Search .................. 604/22, 604/113, 114, 41, 19–21; 607/2, 3, 152; 600/391, 372; 606/27–32, 35, 38
See application file for complete search history.

(56) References Cited

U.S. PATENT DOCUMENTS 2,050,904 A 8/1936 Trice
2,056,377 A 10/1939 Wappler ..................... 125/303

(Continued)

FOREIGN PATENT DOCUMENTS

DE 3930451 3/1991

(Continued)

OTHER PUBLICATIONS

Buchelt, M. et al. "Excimer Laser Ablation of Fibrocartilage: An In Vitro and In Vivo Study," (1991) Lasers in Surgery and Medicine 11:271-279.

(Continued)

*Primary Examiner*—Manuel A Mendez
(74) *Attorney, Agent, or Firm*—Matthew Scheele; Brian E. Szymczak

(57) ABSTRACT

The present invention provides systems, apparatus and methods for removing the outer layer, or stratum corneum, of a patient's skin. In one aspect of the invention, a method includes positioning an active electrode adjacent to or near a target site on a patient's outer skin, and applying a sufficient high frequency voltage to the active electrode to remove the stratum corneum without removing the entire epidermis layer. In this manner, the present invention removes dead and/or damaged skin cells on the surface of the skin which improves the overall appearance of the skin. In addition, this process helps to stimulate the bodies own rejuvenation process. In some embodiments, this rejuvenation process occurs by the actual removal of the stratum corneum, which accelerates the regrowth of new cell layers in the skin. In other embodiments, thermal energy is applied to the underlying epidermis and/or dermis to stimulate the growth of new collagen. In both of these embodiments, the skin appears healthier and, in some cases, small wrinkles are removed or reduced.

23 Claims, 18 Drawing Sheets

U.S. PATENT DOCUMENTS

| | | | |
|---|---|---|---|
| 2,275,167 A | 3/1942 | Bierman | 123/363 |
| 3,301,258 A | 1/1967 | Werner et al. | 128/303 |
| 3,633,425 A | 1/1972 | Sanford | 73/356 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,033,351 A | 7/1977 | Hetzel | 128/303 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 600/505 |
| 4,248,231 A | 2/1981 | Herczog et al. | 128/303 |
| 4,326,529 A | 4/1982 | Doss | 128/303.1 |
| 4,381,007 A | 4/1983 | Doss | 128/303.1 |
| 4,474,179 A | 10/1984 | Koch | 606/40 |
| 4,476,862 A | 10/1984 | Pao | 128/303.17 |
| 4,517,975 A | 5/1985 | Garito et al. | 606/41 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303.13 |
| 4,590,934 A | 5/1986 | Malis et al. | 128/303 |
| 4,593,691 A | 6/1986 | Lindstrom et al. | 128/303.14 |
| 4,658,817 A | 4/1987 | Hardy | 128/303 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,736,743 A | 4/1988 | Daikuzono | 128/303.1 |
| 4,737,678 A | 4/1988 | Hasegawa | 313/36 |
| 4,762,125 A | 8/1988 | Leiman et al. | 128/207 |
| 4,762,128 A | 8/1988 | Rosenbluth | 128/343 |
| 4,762,806 A | 8/1988 | Suzuki et al. | 438/186 |
| 4,765,331 A | 8/1988 | Petruzzi et al. | 128/303 |
| 4,785,806 A | 11/1988 | Deckelbaum | 128/303.1 |
| 4,785,823 A | 11/1988 | Eggers et al. | 128/692 |
| 4,799,480 A | 1/1989 | Abraham et al. | 128/303 |
| 4,805,616 A | 2/1989 | Pao | 128/303 |
| 4,813,429 A | 3/1989 | Eshel et al. | 600/549 |
| 4,823,791 A | 4/1989 | D'amelio | 123/303 |
| 4,832,048 A | 5/1989 | Cohen | 128/786 |
| 4,860,752 A | 8/1989 | Turner | 128/422 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,944,302 A | 7/1990 | Hernandez et al. | 607/76 |
| 4,955,377 A | 9/1990 | Lennox et al. | 128/401 |
| 4,966,597 A | 10/1990 | Cosman | 606/50 |
| 4,967,765 A | 11/1990 | Turner et al. | 128/785 |
| 4,968,314 A | 11/1990 | Michaels | 606/7 |
| 4,976,709 A | 12/1990 | Sand | 606/5 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,437 A | 4/1991 | Sterzer | 428/786 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,037,421 A | 8/1991 | Boutacoff et al. | 606/15 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,059,192 A | 10/1991 | Zaias | 606/9 |
| 5,061,266 A | 10/1991 | Hakky | 606/15 |
| 5,065,515 A | 11/1991 | Iderosa | 30/140 |
| 5,078,717 A | 1/1992 | Parins et al. | 606/48 |
| 5,080,660 A | 1/1992 | Buelna | 606/48 |
| 5,083,565 A | 1/1992 | Parins | 128/642 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E * | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,143,063 A | 9/1992 | Fellner | 128/399 |
| 5,147,354 A | 9/1992 | Boutacoff et al. | 606/15 |
| 5,151,098 A | 9/1992 | Loertscher | 606/16 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,176,528 A | 1/1993 | Fry et al. | 439/181 |
| 5,178,620 A | 1/1993 | Eggers et al. | 606/41 |
| 5,182,857 A | 2/1993 | Simon | 30/34 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,455 A | 6/1993 | Tan | 606/9 |
| 5,217,457 A | 6/1993 | Delahuerga et al. | 606/42 |
| 5,217,459 A | 6/1993 | Kamerling | 606/48 |
| 5,226,907 A | 7/1993 | Tankovich | 606/133 |
| 5,230,334 A | 7/1993 | Klopotek | 601/3 |
| 5,231,984 A | 8/1993 | Santana-Blank | 128/395 |
| 5,241,972 A | 9/1993 | Bonati | 128/898 |
| 5,246,438 A * | 9/1993 | Langberg | 606/33 |
| 5,249,585 A | 10/1993 | Turner et al. | 607/99 |
| 5,261,410 A | 11/1993 | Alfano et al. | 128/664 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,282,797 A | 2/1994 | Chess | 606/9 |
| 5,287,380 A | 2/1994 | Hsia | 372/69 |
| 5,290,273 A | 3/1994 | Tan | 606/9 |
| 5,290,282 A | 3/1994 | Casscells | 606/29 |
| 5,295,955 A | 3/1994 | Rosen et al. | 604/22 |
| 5,300,069 A | 4/1994 | Hunsberger et al. | 606/37 |
| 5,300,099 A | 4/1994 | Rudie | 607/101 |
| 5,301,687 A | 4/1994 | Wong et al. | 607/116 |
| 5,304,169 A | 4/1994 | Sand | 606/5 |
| 5,304,170 A | 4/1994 | Green | 606/9 |
| 5,306,238 A | 4/1994 | Fleenor | 606/42 |
| 5,312,395 A | 5/1994 | Tan et al. | 606/9 |
| 5,312,400 A | 5/1994 | Bales et al. | 606/41 |
| 5,314,406 A | 5/1994 | Arias et al. | 604/21 |
| 5,320,618 A | 6/1994 | Gustafsson | 606/9 |
| 5,322,507 A | 6/1994 | Costello et al. | 128/4 |
| 5,324,254 A | 6/1994 | Phillips | 604/21 |
| 5,329,943 A | 7/1994 | Johnson | 128/898 |
| 5,330,470 A | 7/1994 | Hagen | 606/42 |

| Patent No. | Kind | Date | Inventor | Class |
|---|---|---|---|---|
| 5,330,518 | A | 7/1994 | Neilson et al. | 607/101 |
| 5,334,140 | A | 8/1994 | Phillips | 604/35 |
| 5,334,183 | A | 8/1994 | Wuchinich | 606/46 |
| 5,336,217 | A | 8/1994 | Buys et al. | 606/9 |
| 5,336,220 | A | 8/1994 | Ryan et al. | 604/22 |
| 5,336,443 | A | 8/1994 | Eggers | 252/511 |
| 5,342,357 | A | 8/1994 | Nardella | 606/40 |
| 5,360,447 | A | 11/1994 | Koop | 623/15 |
| 5,366,443 | A | 11/1994 | Eggers et al. | 606/114 |
| 5,370,642 | A | 12/1994 | Keller | 606/9 |
| 5,370,675 | A | 12/1994 | Edwards et al. | 607/101 |
| 5,374,261 | A | 12/1994 | Yoon | 604/385.01 |
| 5,374,265 | A | 12/1994 | Sand | 606/5 |
| 5,375,588 | A | 12/1994 | Yoon | 128/4 |
| 5,380,277 | A | 1/1995 | Phillips | 604/33 |
| 5,380,316 | A | 1/1995 | Aita et al. | 606/7 |
| 5,383,876 | A | 1/1995 | Nardella | 606/49 |
| 5,383,917 | A | 1/1995 | Desai et al. | 607/702 |
| 5,389,096 | A | 2/1995 | Aita et al. | 606/15 |
| 5,395,312 | A | 3/1995 | Desai | 604/22 |
| 5,400,267 | A | 3/1995 | Denen et al. | 702/59 |
| 5,401,272 | A | 3/1995 | Perkins | 606/15 |
| 5,403,311 | A | 4/1995 | Abele et al. | 606/49 |
| 5,417,687 | A | 5/1995 | Nardella et al. | 606/32 |
| 5,419,767 | A | 5/1995 | Eggers et al. | 604/114 |
| 5,423,803 | A | 6/1995 | Tankovich | 606/9 |
| 5,423,810 | A | 6/1995 | Goble et al. | 606/40 |
| 5,423,882 | A | 6/1995 | Jackman et al. | 607/122 |
| 5,425,728 | A | 6/1995 | Tankovich | 606/9 |
| 5,433,708 | A | 7/1995 | Nichols et al. | 604/113 |
| 5,436,566 | A | 7/1995 | Thompson et al. | 324/713 |
| 5,437,662 | A | 8/1995 | Nardella | 606/40 |
| 5,438,302 | A | 8/1995 | Goble | 331/167 |
| 5,441,499 | A | 8/1995 | Fritzsch | 606/45 |
| 5,445,634 | A | 8/1995 | Keller | 606/9 |
| 5,449,378 | A | 9/1995 | Schouenborg | 607/46 |
| 5,451,224 | A | 9/1995 | Goble et al. | 606/48 |
| 5,454,809 | A | 10/1995 | Janssen | 606/41 |
| 5,458,597 | A | 10/1995 | Edwards et al. | 606/41 |
| 5,472,441 | A | 12/1995 | Edwards et al. | 606/41 |
| 5,484,435 | A | 1/1996 | Fleenor et al. | 606/46 |
| 5,490,850 | A | 2/1996 | Ellman et al. | 606/45 |
| 5,496,312 | A | 3/1996 | Klicek | 606/34 |
| 5,496,314 | A | 3/1996 | Eggers | 606/41 |
| 5,496,317 | A | 3/1996 | Goble et al. | 606/48 |
| 5,505,727 | A | 4/1996 | Keller | 606/9 |
| 5,507,790 | A | 4/1996 | Weiss | 607/101 |
| 5,514,130 | A | 5/1996 | Baker | 606/41 |
| 5,522,813 | A | 6/1996 | Trelles | 606/2 |
| 5,554,152 | A | 9/1996 | Aita | 606/7 |
| 5,556,397 | A | 9/1996 | Long et al. | 606/48 |
| 5,569,242 | A | 10/1996 | Lax et al. | 606/42 |
| 5,571,100 | A | 11/1996 | Goble et al. | 606/41 |
| 5,578,029 | A | 11/1996 | Trelles et al. | 606/25 |
| 5,584,872 | A | 12/1996 | LaFontaine et al. | 607/116 |
| 5,609,151 | A | 3/1997 | Mulier et al. | 128/642 |
| 5,611,795 | A | 3/1997 | Slatkine et al. | 606/9 |
| 5,626,576 | A | 5/1997 | Janssen | 606/41 |
| 5,633,578 | A | 5/1997 | Eggers et al. | 323/301 |
| 5,647,869 | A | 7/1997 | Goble et al. | 606/37 |
| 5,660,836 | A | 8/1997 | Knowlton | 424/400 |
| 5,662,680 | A | 9/1997 | Desai | 606/210 |
| 5,676,693 | A | 10/1997 | LaFontaine et al. | 607/116 |
| 5,681,282 | A | 10/1997 | Eggers et al. | 604/114 |
| 5,683,366 | A | 11/1997 | Eggers et al. | 604/114 |
| 5,683,386 | A | 11/1997 | Ellman et al. | 606/41 |
| 5,683,387 | A | 11/1997 | Garito et al. | 606/45 |
| 5,695,495 | A | 12/1997 | Ellman et al. | 606/41 |
| 5,697,281 | A | 12/1997 | Eggers et al. | 604/114 |
| 5,697,536 | A | 12/1997 | Eggers et al. | 604/114 |
| 5,697,882 | A | 12/1997 | Eggers et al. | 604/114 |
| 5,697,909 | A | 12/1997 | Eggers et al. | 604/114 |
| 5,700,262 | A | 12/1997 | Acosta et al. | 606/48 |
| 5,725,524 | A | 3/1998 | Mulier et al. | 606/41 |
| 5,746,746 | A | 5/1998 | Garito et al. | 606/41 |
| 5,749,869 | A | 5/1998 | Lindenmeier et al. | 606/34 |
| 5,755,753 | A | 5/1998 | Knowlton | 607/98 |
| 5,766,153 | A | 6/1998 | Eggers et al. | 604/114 |
| 5,769,847 | A | 6/1998 | Panescu et al. | 606/42 |
| 5,807,385 | A | 9/1998 | Keller | 606/9 |
| 5,807,395 | A | 9/1998 | Mulier et al. | 606/41 |
| 5,810,764 | A | 9/1998 | Eggers et al. | 604/23 |
| 5,810,802 | A | 9/1998 | Panescu et al. | 606/31 |
| 5,810,809 | A | 9/1998 | Rydell | 606/49 |
| 5,814,042 | A | 9/1998 | Zair | 606/17 |
| 5,836,875 | A | 11/1998 | Webster, Jr. | 600/374 |
| 5,843,019 | A | 12/1998 | Eggers et al. | 604/22 |
| 5,843,078 | A | 12/1998 | Sharkey | |
| 5,860,951 | A | 1/1999 | Eggers et al. | 604/49 |
| 5,860,974 | A | 1/1999 | Abele | 606/41 |
| 5,860,975 | A | 1/1999 | Goble et al. | 606/45 |
| 5,868,744 | A | 2/1999 | Willmen | 606/50 |
| 5,871,469 | A | 2/1999 | Eggers et al. | 604/114 |
| 5,873,855 | A | 2/1999 | Eggers et al. | 604/114 |
| 5,885,277 | A | 3/1999 | Korth | 606/35 |
| 5,888,198 | A | 3/1999 | Eggers et al. | 604/114 |
| 5,891,095 | A | 4/1999 | Eggers et al. | 604/114 |
| 5,891,134 | A | 4/1999 | Goble et al. | 606/27 |
| 5,897,553 | A | 4/1999 | Mulier et al. | 606/41 |
| 5,902,272 | A | 5/1999 | Eggers et al. | 604/114 |
| 5,931,807 | A | 8/1999 | McClure et al. | 604/27 |
| 5,944,715 | A | 8/1999 | Goble et al. | 606/41 |
| 5,947,964 | A | 9/1999 | Eggers et al. | 604/114 |
| 5,948,011 | A | 9/1999 | Knowlton | 607/101 |
| 5,954,716 | A | 9/1999 | Sharkey et al. | 606/32 |
| 6,004,319 | A | 12/1999 | Goble et al. | 606/48 |
| 6,013,076 | A | 1/2000 | Goble et al. | 606/41 |
| 6,015,406 | A | 1/2000 | Goble et al. | 606/41 |
| 6,024,733 | A | 2/2000 | Eggers et al. | 604/500 |
| 6,027,501 | A | 2/2000 | Goble et al. | 606/41 |
| 6,039,734 | A | 3/2000 | Goble et al. | 606/41 |
| 6,047,215 | A | 4/2000 | McClure | 607/101 |
| 6,047,700 | A | 4/2000 | Eggers et al. | 128/898 |
| 6,056,746 | A | 5/2000 | Goble et al. | 606/48 |
| 6,063,079 | A | 5/2000 | Hovda et al. | 606/41 |
| 6,066,134 | A | 5/2000 | Eggers et al. | 606/32 |
| 6,068,628 | A | 5/2000 | Fanton et al. | 606/41 |
| 6,074,386 | A | 6/2000 | Goble et al. | 606/34 |
| 6,090,106 | A | 7/2000 | Goble et al. | 606/41 |
| 6,093,186 | A | 7/2000 | Goble et al. | 606/34 |
| 6,102,046 | A | 8/2000 | Weinstein et al. | 128/898 |
| 6,102,885 | A | 8/2000 | Bass | 604/22 |
| 6,105,581 | A | 8/2000 | Eggers et al. | 128/898 |
| 6,106,521 | A | 8/2000 | Blewett et al. | 606/41 |
| 6,109,268 | A | 8/2000 | Thapliyal et al. | 128/898 |
| 6,117,109 | A | 9/2000 | Eggers et al. | 604/114 |
| 6,126,682 | A | 10/2000 | Sharkey et al. | 607/96 |
| 6,142,992 | A | 11/2000 | Cheng et al. | 606/34 |
| 6,148,232 | A * | 11/2000 | Avrahami | 604/20 |
| 6,149,620 | A | 11/2000 | Baker et al. | 604/22 |
| 6,159,194 | A | 12/2000 | Eggers et al. | 604/500 |
| 6,159,208 | A | 12/2000 | Hovda et al. | 606/41 |
| 6,168,593 | B1 | 1/2001 | Sharkey et al. | 606/34 |
| 6,174,309 | B1 | 1/2001 | Wrublewski et al. | 606/45 |
| 6,179,824 | B1 | 1/2001 | Eggers et al. | 604/500 |
| 6,179,836 | B1 | 1/2001 | Eggers et al. | 606/45 |
| 6,183,469 | B1 | 2/2001 | Thapliyal et al. | 606/41 |
| 6,190,381 | B1 | 2/2001 | Olsen et al. | 606/32 |
| 6,203,542 | B1 | 3/2001 | Ellsberry et al. | 606/41 |
| 6,210,402 | B1 | 4/2001 | Olsen et al. | 606/32 |
| 6,224,592 | B1 | 5/2001 | Eggers et al. | 606/32 |
| 6,228,078 | B1 | 5/2001 | Eggers | 606/32 |
| 6,228,081 | B1 | 5/2001 | Goble | 606/34 |
| 6,228,082 | B1 | 5/2001 | Baker et al. | 606/49 |
| 6,235,020 | B1 | 5/2001 | Cheng et al. | 606/34 |
| 6,237,604 | B1 | 5/2001 | Burnside et al. | 128/897 |

| | | | | | | |
|---|---|---|---|---|---|---|
| 6,238,391 B1 | 5/2001 | Olsen et al. ............... 606/41 | | 7,270,659 B2 | 9/2007 | Hovda et al. ............... 606/32 |
| 6,254,600 B1 | 7/2001 | Willink et al. ............ 606/41 | | 7,270,661 B2 | 9/2007 | Dahla et al. ............... 606/41 |
| 6,261,286 B1 | 7/2001 | Goble et al. ............... 606/34 | | 7,276,063 B2 | 10/2007 | Davison et al. ............ 606/45 |
| 6,261,311 B1 | 7/2001 | Sharkey et al. ............ 607/96 | | 7,297,143 B2 | 11/2007 | Woloszko et al. .......... 606/41 |
| 6,264,652 B1 | 7/2001 | Eggers et al. ............. 606/41 | | 7,297,145 B2 | 11/2007 | Ormsby et al. ............ 606/41 |
| 6,270,460 B1 | 8/2001 | McCartan et al. ......... 600/459 | | 7,318,823 B2 | 1/2008 | Sharps et al. ............. 606/32 |
| 6,277,112 B1 | 8/2001 | Underwood et al. ...... 606/32 | | 7,331,956 B2 | 2/2008 | Hovda et al. ............... 606/32 |
| 6,277,116 B1 | 8/2001 | Utely et al. ............... 606/42 | | RE40,156 E | 3/2008 | Sharps et al. ............. 606/32 |
| 6,280,441 B1 | 8/2001 | Ryan ........................ 606/45 | | 7,357,798 B2 | 4/2008 | Sharps et al. ............. 606/32 |
| 6,283,987 B1 | 9/2001 | Laird ........................ 607/96 | | 7,387,625 B2 | 6/2008 | Hovda et al. ............... 606/32 |
| 6,293,942 B1 | 9/2001 | Goble et al. ............... 606/38 | | 7,419,488 B2 | 9/2008 | Ciarrocca et al. .......... 606/41 |
| 6,296,636 B1 | 10/2001 | Cheng et al. ............. 606/32 | | 7,429,260 B2 | 9/2008 | Underwood et al. ...... 606/32 |
| 6,296,638 B1 | 10/2001 | Davison et al. ............ 606/41 | | 7,429,262 B2 | 9/2008 | Woloszko et al. .......... 606/46 |
| 6,306,134 B1 | 10/2001 | Goble et al. ............... 606/42 | | 7,435,247 B2 | 10/2008 | Woloszko et al. .......... 604/45 |
| 6,308,089 B1 | 10/2001 | von der Rur et al. ...... 600/338 | | 2002/0029036 A1 | 3/2002 | Goble et al. ............... 606/38 |
| 6,309,387 B1 | 10/2001 | Eggers et al. ............. 606/41 | | 2002/0095151 A1 | 7/2002 | Dahla et al. ............... 606/41 |
| 6,312,408 B1 | 11/2001 | Eggers et al. ............. 604/114 | | 2002/0120260 A1 | 8/2002 | Morris et al. ............. 606/41 |
| 6,312,428 B1 | 11/2001 | Eggers et al. ............. 606/41 | | 2003/0013986 A1 | 1/2003 | Saadat ...................... 600/549 |
| 6,322,549 B1 | 11/2001 | Eggers et al. ............. 604/500 | | 2003/0028189 A1 | 2/2003 | Woloszko et al. .......... 604/45 |
| 6,355,032 B1 | 3/2002 | Hovda et al. ............... 606/32 | | 2003/0088245 A1 | 5/2003 | Woloszko et al. .......... 606/41 |
| 6,363,937 B1 | 4/2002 | Hovda et al. ............... 128/898 | | 2003/0158545 A1 | 8/2003 | Hovda et al. ............... 606/32 |
| 6,364,877 B1 | 4/2002 | Goble et al. ............... 606/34 | | 2003/0171743 A1 | 9/2003 | Tasto et al. ............... 606/32 |
| 6,379,351 B1 | 4/2002 | Thapliyal et al. .......... 606/41 | | 2003/0208194 A1 | 11/2003 | Hovda et al. ............... 606/41 |
| 6,383,184 B1 | 5/2002 | Sharkey ..................... 606/41 | | 2003/0208196 A1 | 11/2003 | Stone ........................ 606/41 |
| 6,391,023 B1 | 5/2002 | Weber et al. .............. 606/15 | | 2003/0212395 A1 | 11/2003 | Woloszko et al. .......... 606/32 |
| 6,391,025 B1 | 5/2002 | Weinstein et al. .......... 606/41 | | 2003/0212396 A1 | 11/2003 | Eggers et al. ............. 606/41 |
| 6,416,507 B1 | 7/2002 | Eggers et al. ............. 606/32 | | 2004/0024399 A1 | 2/2004 | Sharps et al. ............. 606/32 |
| 6,416,508 B1 | 7/2002 | Eggers et al. ............. 606/32 | | 2004/0049180 A1 | 3/2004 | Sharps et al. ............. 606/32 |
| 6,416,509 B1 | 7/2002 | Goble et al. ............... 606/37 | | 2004/0054366 A1 | 3/2004 | Davison et al. ............ 606/45 |
| 6,416,514 B1 | 7/2002 | Ein-Gal ..................... 606/49 | | 2004/0116922 A1 | 6/2004 | Hovda et al. ............... 606/41 |
| 6,432,103 B1 | 8/2002 | Ellsberry et al. ........... 606/41 | | 2004/0127893 A1 | 7/2004 | Hovda ...................... 606/41 |
| 6,461,350 B1 | 10/2002 | Underwood et al. ...... 606/32 | | 2004/0153057 A1 | 8/2004 | Davison .................... 600/410 |
| 6,468,274 B1 | 10/2002 | Alleyne et al. ............ 606/32 | | 2004/0186469 A1 | 9/2004 | Woloszko et al. .......... 606/41 |
| 6,468,275 B1 | 10/2002 | Wampler et al. .......... 606/48 | | 2004/0230190 A1 | 11/2004 | Dahla et al. ............... 604/41 |
| 6,482,201 B1 | 11/2002 | Olsen et al. ............... 606/41 | | 2005/0004634 A1 | 1/2005 | Hovda et al. ............... 606/41 |
| 6,517,498 B1 | 2/2003 | Burbank et al. ........... 600/564 | | 2005/0010205 A1 | 1/2005 | Hovda et al. ............... 606/32 |
| 6,530,922 B2 | 3/2003 | Cosman .................... 606/34 | | 2005/0119650 A1 | 6/2005 | Sanders et al. ............ 424/426 |
| 6,578,579 B2 | 6/2003 | Burnside .................... 128/897 | | 2005/0131402 A1 | 6/2005 | Ciarrocca et al. .......... 600/450 |
| 6,589,237 B2 | 7/2003 | Woloszko et al. .......... 606/41 | | 2005/0187543 A1 | 8/2005 | Underwood et al. ...... 606/41 |
| 6,602,248 B1 | 8/2003 | Sharps et al. ............. 606/32 | | 2005/0234439 A1 | 10/2005 | Underwood et al. ...... 606/32 |
| 6,620,156 B1 | 9/2003 | Garito et al. .............. 606/50 | | 2005/0251134 A1 | 11/2005 | Woloszko et al. .......... 606/32 |
| 6,632,193 B1 | 10/2003 | Davison et al. ............ 604/22 | | 2005/0261754 A1 | 11/2005 | Woloszko et al. .......... 606/32 |
| 6,632,220 B1 | 10/2003 | Eggers et al. ............. 606/41 | | 2005/0288665 A1 | 12/2005 | Woloszko et al. .......... 606/41 |
| 6,749,604 B1 | 6/2004 | Eggers et al. ............. 606/41 | | 2006/0036237 A1 | 2/2006 | Davison et al. ............ 606/41 |
| 6,749,608 B2 | 6/2004 | Garito et al. .............. 606/45 | | 2006/0095026 A1 | 5/2006 | Hovda et al. ............... 606/32 |
| 6,770,071 B2 | 8/2004 | Woloszko et al. .......... 606/41 | | 2006/0095031 A1 | 5/2006 | Ormsby .................... 606/34 |
| 6,773,431 B2 | 8/2004 | Eggers et al. ............. 606/32 | | 2006/0129145 A1 | 6/2006 | Ormsby et al. ............ 606/41 |
| 6,780,178 B2 | 8/2004 | Palanker et al. ........... 600/41 | | 2006/0178670 A1 | 8/2006 | Woloszko et al. .......... 606/48 |
| 6,780,180 B1 | 8/2004 | Goble et al. ............... 606/41 | | 2006/0189971 A1 | 8/2006 | Eggers et al. ............. 606/32 |
| 6,802,842 B2 | 10/2004 | Ellman et al. .............. 606/45 | | 2006/0253117 A1 | 11/2006 | Hovda et al. ............... 128/898 |
| 6,837,887 B2 | 1/2005 | Woloszko et al. .......... 606/41 | | 2006/0259025 A1 | 11/2006 | Dahla ...................... 607/108 |
| 6,837,888 B2 | 1/2005 | Ciarrocca et al. .......... 606/41 | | 2007/0010808 A1 | 1/2007 | Dahla ...................... 606/41 |
| 6,920,883 B2 | 7/2005 | Bessette et al. ............ 128/898 | | 2007/0010809 A1 | 1/2007 | Sanders et al. ............ 606/32 |
| 6,929,640 B1 | 8/2005 | Underwood et al. ...... 606/32 | | 2007/0106288 A1 | 5/2007 | Woloszko et al. .......... 606/41 |
| 6,949,096 B2 | 9/2005 | Davison et al. ............ 606/41 | | 2007/0112348 A1 | 5/2007 | Eggers et al. ............. 606/41 |
| 6,960,204 B2 | 11/2005 | Eggers et al. ............. 606/32 | | 2007/0129715 A1 | 6/2007 | Eggers et al. ............. 606/32 |
| 6,974,453 B2 | 12/2005 | Woloszko et al. .......... 606/41 | | 2007/0149966 A1 | 6/2007 | Dahla et al. ............... 606/41 |
| 6,984,231 B2 | 1/2006 | Goble et al. ............... 606/37 | | 2007/0161981 A1 | 7/2007 | Sanders et al. ............ 606/41 |
| 6,991,631 B2 | 1/2006 | Woloszko et al. .......... 606/41 | | 2007/0179497 A1 | 8/2007 | Eggers et al. ............. 606/41 |
| 7,004,941 B2 | 2/2006 | Tvinnereim et al. ....... 606/41 | | 2007/0208334 A1 | 9/2007 | Woloszko et al. .......... 606/41 |
| 7,041,102 B2 | 5/2006 | Truckai et al. ............. 606/51 | | 2007/0208335 A1 | 9/2007 | Woloszko et al. .......... 606/41 |
| 7,070,596 B1 | 7/2006 | Woloszko et al. .......... 606/41 | | 2007/0213700 A1 | 9/2007 | Davison et al. ............ 606/32 |
| 7,090,672 B2 | 8/2006 | Underwood et al. ...... 606/41 | | 2007/0282323 A1 | 12/2007 | Woloszko et al. .......... 606/41 |
| 7,094,215 B2 | 8/2006 | Davison et al. ............ 604/22 | | | | |
| 7,104,986 B2 | 9/2006 | Hovda et al. ............... 606/32 | | | FOREIGN PATENT DOCUMENTS | |
| 7,131,969 B1 | 11/2006 | Hovda et al. ............... 606/45 | | | | |
| 7,169,143 B2 | 1/2007 | Eggers et al. ............. 606/32 | | DE | 44 25 015 | 1/1996 |
| 7,179,255 B2 | 2/2007 | Lettice et al. ............. 606/32 | | EP | 480639 | 4/1992 |
| 7,186,234 B2 | 3/2007 | Dahla et al. ............... 604/22 | | EP | 515 867 | 12/1992 |
| 7,192,428 B2 | 3/2007 | Eggers et al. ............. 606/41 | | EP | 0 597 463 | 5/1994 |
| 7,201,750 B1 | 4/2007 | Eggers et al. ............. 606/41 | | EP | 0 703 461 | 3/1996 |
| 7,217,268 B2 | 5/2007 | Eggers et al. ............. 606/32 | | EP | 0 703 461 A2 | 3/1996 |
| 7,270,658 B2 | 9/2007 | Woloszko et al. .......... 606/32 | | EP | 0 740 926 | 11/1996 |

| | | |
|---|---|---|
| EP | 0 740 926 A2 | 11/1996 |
| EP | 0 754 437 | 1/1997 |
| EP | 0 694 290 | 11/2000 |
| FR | 2313949 | 1/1977 |
| GB | 2 308 979 | 7/1997 |
| GB | 2 308 980 | 7/1997 |
| GB | 2 308 981 | 7/1997 |
| GB | 2308979 | 7/1997 |
| GB | 2308980 | 7/1997 |
| GB | 2308981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| NL | 05/000434 | 12/2006 |
| WO | 90/03152 | 4/1990 |
| WO | 90/07303 | 7/1990 |
| WO | WO 90/07303 | 7/1990 |
| WO | WO 91/13650 | 9/1991 |
| WO | 92/21278 | 12/1992 |
| WO | WO 92/21278 | 12/1992 |
| WO | 93/13816 | 7/1993 |
| WO | WO 93/13816 | 7/1993 |
| WO | 93/20747 | 10/1993 |
| WO | 94/04220 | 3/1994 |
| WO | WO 94/04220 | 3/1994 |
| WO | 94/08654 | 4/1994 |
| WO | WO 94/14383 | 7/1994 |
| WO | WO 94/26228 | 11/1994 |
| WO | 95/34259 | 12/1995 |
| WO | 96/00042 | 1/1996 |
| WO | 96/32051 | 10/1996 |
| WO | 96/34568 | 11/1996 |
| WO | 97/00646 | 1/1997 |
| WO | 97/00647 | 1/1997 |
| WO | 97/15238 | 5/1997 |
| WO | 97/24073 | 7/1997 |
| WO | 97/24074 | 7/1997 |
| WO | 97/24992 | 7/1997 |
| WO | 97/24993 | 7/1997 |
| WO | 97/24994 | 7/1997 |
| WO | 97/48345 | 12/1997 |
| WO | 97/48346 | 12/1997 |
| WO | 98/07468 | 2/1998 |
| WO | 98/11944 | 3/1998 |
| WO | 98/27879 | 7/1998 |
| WO | 98/27880 | 7/1998 |
| WO | 98/38936 | 9/1998 |
| WO | 98/44968 | 10/1998 |
| WO | 99/51155 | 10/1999 |
| WO | 99/51158 | 10/1999 |
| WO | 01/87154 | 5/2001 |
| WO | 02/36028 | 5/2002 |
| WO | 2005/125287 | 12/2005 |

OTHER PUBLICATIONS

Costello, A. J. et al. "Nd:YAG Laser Ablation of the Prostate as a Treatment of Benign Prostatic Hypertrophy," (1992) Lasers in Surger and Medicine 12:121-124.
Rand et al. (1985) *J. Arthro Surg.* 1:242-246 Effect of Electrocautery on Fresh Human Articular Cartilage.
E. Kramolowsky et al. (1991) *J. of Urology* 146:669-674.
J. Pearce *Electrosurgery*, (1986) John Wiley & Sons, New York, pp. 17, 69-75 and 87.
Slager et al. (1985) *JACC* 5(6): 1382-6.
Slager et al. (1987) *Z. Kardiol.* 76:Suppl. 6, 67-71.
Pearce, John A. (1986) *Electrosurgery*, pp. 17, 69-75, 87, John Wiley & Sons, New York.
J.W. Ramsey et al. *Urological Research* vol. 13, pp. 99-102 (1985).
V.E. Elsasser et al. *Acta Medicotechnica* vol. 24, No. 4, pp. 129-134 (1976).

P.C. Nardella (1989) *SPIE* 1068:42-49 Radio Frequency Energy and Impedance Feedback.
R. Tucker et al., Abstract P14-11, p. 248, "A Bipolar Electrosurgical Turp Loop".
R. Tucker et al. *J. of Urology* vol. 141, pp. 662-665, (1989).
R. Tucker et al. *Urological Research* vol. 18, pp. 291-294 (1990).
Kramolowsky et al. *J. of Urology* vol. 143, pp. 275-277 (1990).
Kramolowsky et al. *J. of Urology* vol. 146, pp. 669-674 (1991).
Slager et al. *Z. Kardiol.* 76:Suppl. 6, 67-71 (1987).
Slager et al. *JACC* 5(6):1382-6 (1985).
Olsen MD, Bipolar Laparoscopic Cholecstectomy Lecture (marked confidential), Oct. 7, 1991.
Codman & Shurtleff, Inc. "The Malis Bipolar Electrosurgical System CMC-III Instruction Manual" Jul. 1991.
Valley Forge's New Products, CLINICA, 475, 5, Nov. 6, 1991.
Valley Forge Scientific Corp., "Summary of Safety and Effective Information from 510K," 1991.
Codman & Shurtleff, Inc. "The Malis Bipolar Coagulating and Bipolar Cutting System CMC-II" brochure, early 1991.
L. Malis, "The Value of Irrigation During Bipolar Coagulation" See ARTC 21602, early Apr. 9, 1993.
L. Malis, "Excerpted from a seminar by Leonard I. Malis, M.D. at the 1995 American Association of Neurological Surgeons Meeting," 1995.
L. Malis, "Electrosurgery, Technical Note," *J. Neursurg.*, vol. 85, 970-975, Nov. 1996.
Ian E. Shuman, "Bipolar Versus Monopolar Electrosurgery: Clinical Applications," *Dentistry Today*, vol. 20, No. 12, Dec. 2001.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455.
Cook and Webster, "Therapeutic Medical Devices: Application and Design," 1982.
Valleylab SSE2L Instruction Manual, Jan. 6, 1983.
Robert D. Tucker et al., "Demodulated Low Frequency Currents from Electrosurgical Procedures," *Surgery, Gynecology and Obstetrics*, 159:39-43, 1984.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122.
Selikowitz & LaCourse, "Electric Current and Voltage Recordings on the Myocardium During Electrosurgical Procedures in Canines," *Surgery, Gynecology & Obstetrics*, vol. 164, 219-224, Mar. 1987.
J. O'Malley, Schaum's Outline of Theory and Problems of Basic Circuit Analysis, McGraw-Hill, $2^{nd}$ Ed., 1992, pp. 3-5.
Arnaud Wattiez et al., "Electrosurgery in Operative Endoscopy," Electrosurgical Effects, Blackwell Science, pp. 85-93, 1995.
Leslie A. Geddes, "Medical Device Accidents: With Illustrative Cases" CRC Press, 1998.
Wyeth, "Electrosurgical Unit" pp. 1181-1202.
C.P. Swain, et al., *Gut* vol. 25, pp. 1424-1431 (1984).
Piercey et al., *Gastroenterology* vol. 74(3), pp. 527-534 (1978).
A.K. Dobbie *Bio-Medical Engineering* vol. 4, pp. 206-216 (1969).
B. Lee et al. JACC vol. 13(5), pp. 1167-1175 (1989).
K. Barry et al. *American Heart Journal* vol. 117, pp. 332-341 (1982).
W. Honig *IEEE* pp. 58-65 (1975).
Jacob Kline, *Handbook of Biomedical Engineering*, Academic Press Inc., N.Y., pp. 98-113, 1988.
M.B. Dennis et al. "Evolution of Electrofulguration in Control of Bleeding of Experimental Gastric Ulcers," Digestive Diseases and Sciences, vol. 24, No. 11, 845-848.
Letter from Department of Health to Jerry Malis dated Apr. 15, 1985.
Letter from Jerry Malis to FDA dated Jul. 25, 1985.
Letter from Department of Health to Jerry Malis dated Apr. 22, 1991.
Leonard Malis, "Instrumentation for Microvascular Neurosurgery" *Cerebrovascular Surgery*, vol. 1, 245-260, 1985.
Valleylab, Inc. "Valleylab Part No. 945 100 102 A" Surgistat Service Manual, Jul. 1988.
Leonard I. Malis, "New Trends in Microsurgery and Applied Technology," *Advanced Technology in Neurosurgery*, 1-16, 1988.
European Search Report for EP 98958641, 2pgs, Nov. 9, 2000.
PCT International Search Report for PCT/US98/24654 1 pg, mailed Feb. 10, 1999.

PCT International Search Report for PCT/US99/27866 1 pg, mailed Jan. 21, 2000.

PCT International Search Report for PCT/US00/09506 1 pg, mailed Sep. 27, 2000.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

BiLAP IFU 910026-001 Rev A for BiLAP Model 3525, J-Hook, 4 pgs, May 20, 1991.

BiLAP Generator Settings, Jun. 1991.

Tucker et al. "The interaction between electrosurgical generators, endroscopic electrodes, and tissue," Gastrointestinal Endoscopy, vol. 38, No. 2, pp. 118-122, 1992.

Codman & Shurtleff, Inc. "The Malis Bipolar Coagulating and Bipolar Cutting System CMC-II" brochure, early, 2 pgs, 1991.

Stoffels, E. et al., "Investigation on the Interaction Plasma-Bone Tissue", E-MRS Spring Meeting, 1 pg, June 18-21, 2002.

Stoffels, E. et al., "Biomedical Applications of Plasmas", Tutorial presented prior to the 55$^{th}$ Gaseous Electronics Conference in Minneapolis, MN, 41 pgs, Oct. 14, 2002.

Stoffels, E. et al., "Plasma Interactions with Living Cells", Eindhoven University of Technology, 1 pg, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003.

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1540, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 6, 2006.

US 5,326,343, 07/1994, Rudie et al. (withdrawn)

* cited by examiner

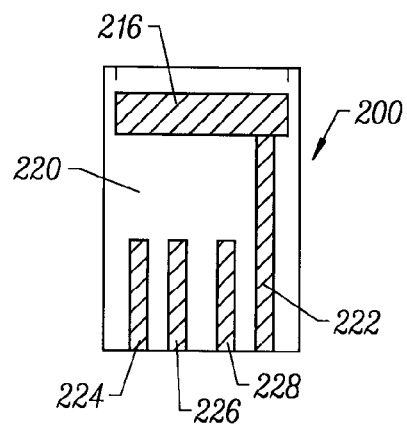
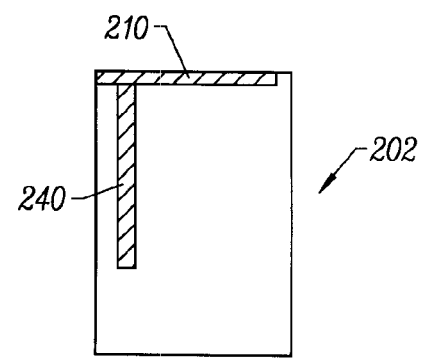
FIG. 9A　　　　　　　　FIG. 10A
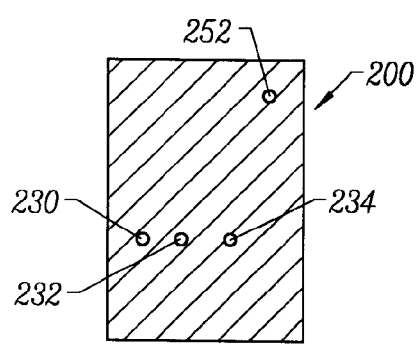
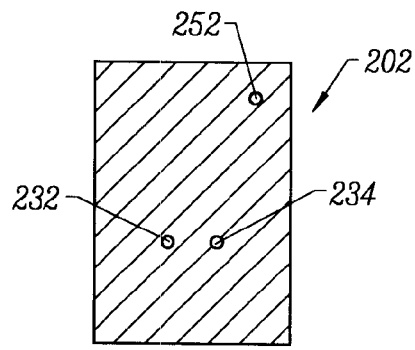
FIG. 9B　　　　　　　　FIG. 10B

SYSTEMS AND METHODS FOR ELECTROSURGICAL REMOVAL OF THE STRATUM CORNEUM

RELATED APPLICATIONS

The present invention is a continuation-in-part of U.S. patent application Ser. Nos. 08/977,845, now U.S. Pat. No. 6,210,402, and 09/248,763, now U.S. Pat. No. 6,149,620, filed Nov. 25, 1997, and Feb. 12, 1999, respectively. U.S. patent application Ser. No. 08/977,845 is a continuation-in-part of U.S. patent application Ser. No. 08/562,332, filed Nov. 22, 1995, now U.S. Pat. No. 6,024,733, the complete disclosures of which are incorporated herein by reference for all purposes.

The present invention is also related to commonly assigned U.S. patent application Ser. No. 08/990,374, filed Dec. 15, 1997, now U.S. Pat. No. 6,109,268, which is a continuation in part of U.S. patent application Ser. No. 08/485,219, filed on Jun. 7, 1995, now U.S. Patent No. 5,697,281, patent application Ser. Nos. 09/109,219, now abandoned, 09/058,571, now U.S. Pat. No. 6,142,992, 08/874,173, now U.S. Pat. No. 6,179,824, and 09/002,315, now U.S. Pat. No. 6,183,469, filed on Jun. 30, 1998, Apr. 10, 1998, Jun. 13, 1997, and Jan. 2, 1998, respectively and U.S. patent application Ser. No. 09/054,323, filed on Apr. 2, 1998, now U.S. Pat. No. 6,063,079, U.S. patent application Ser. No. 09/010,382, filed Jan. 21, 1998, now U.S. Pat. No. 6,190,381, and U.S. patent application Ser. No. 09/032,375, filed Feb. 27, 1998, now U.S. Pat. No. 6,355,032, U.S. application Ser. No. 08/942,580, filed on Oct. 2, 1997, now U.S. Pat. No. 6,159,194, U.S. application Ser. No. 08/753,227, filed on Nov. 22, 1996, now U.S. Pat. No. 5,873,855, U.S. application Ser. No. 08/687,792, filed on Jul. 18, 1996, now U.S. Pat. No. 5,843,019, and PCT International Application, U.S. National Phase Serial No. PCT/US94/05168, filed on May 10, 1994, now U.S. Pat. No. 5,697,909, which was a continuation in part of U.S. patent application Ser. No. 08/059,681, filed on May 10, 1993, now abandoned, which was a continuation in part of U.S. patent application Ser. No. 07/958,977, filed on Oct. 9, 1992, now U.S. Pat. No. 5,366,443, which was a continuation in part of U.S. patent application Ser. No. 07/817,575, filed on Jan. 7, 1992, now abandoned, the complete disclosures of which are incorporated herein by reference for all purposes. The present invention is also related to commonly assigned U.S. patent application Ser. No. 08/561,958, now U.S. Pat. No. 5,697,882, which was filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat a patient's skin and subcutaneous tissue, including skin resurfacing procedures, such as procedures for selectively ablating a thin layer of surface tissue, such as the corneum stratum.

In early dermatology procedures, cosmetic surgeons often employed chemical peels and/or dermabrasion techniques to remove outer layers of the patient's skin to rejuvenate wrinkled skin or to remove skins disorders, such as acne, lesions, early skin cancer, etc. These dermabrasion and chemical procedures, however, are difficult to control, requiring great surgical skill. In addition, these somewhat inelegant techniques often cause excessive bleeding, collateral tissue damage and patient discomfort.

In an effort to overcome some of the limitations of dermabrasion and chemical peels, lasers have been developed for use in cosmetic surgery. Lasers have improved the accuracy of skin resurfacing procedures, and they have reduced collateral damage to the tissue surrounding and underlying the treatment site. In laser dermatology applications, a handpiece is typically used to guide the output of a laser to the patient's skin, and to form a laser spot of a desired size on the region of the skin which is to be treated. The handpiece is typically attached to one end of an articulated arm which transmits the output of a medical laser (such as $CO_2$ or Er: YAG lasers) to the handpiece and allows the handpiece a wide range of motion.

Although initially encouraging, lasers suffer from a number of drawbacks in dermatology procedures. In the first place, laser equipment can be very expensive because of the costs associated with the laser light sources. Moreover, those lasers which permit acceptable depths of necrosis (such as excimer lasers, erbium:YAG lasers, and the like) provide a very low volumetric ablation rate, requiring numerous passes over the same treatment area which amounts to longer procedural times. In addition, erbium:YAG lasers generally do not provide effective hemostasis during the procedure, resulting in excessive bleeding which disrupts the surgeon's view of the treatment site. The $CO_2$ lasers provide a higher rate of ablation and an increased depth of tissue necrosis than their erbium: YAG counterparts. On the other hand, $CO_2$ lasers often create significant residual thermal injury to tissue at and surrounding the treatment site, which requires long healing periods for the patient. In addition, $CO_2$ lasers are associated with much pain and, therefore, require a lot of anesthesia, which increases the cost and length of the procedure.

Monopolar electrosurgical instruments have been used to effect electro-dessication of abnormalities, such as lesions, skin tags, viral warts, pigment nevi, moles and skin cancer. For example, Conmed Corporation manufacturers a monopolar device, termed the Hyfrecator™ having a single active electrode at the tip of an electrosurgical probe. In these procedures, the skin abnormality is typically removed with a scalpel, and a low voltage is applied to the active electrode in contact with the target tissue to deliver electric current through the tissue and the patient to a dispersive pad or indifferent electrode. The voltage desiccates the remaining abnormal tissue, and coagulates severed blood vessels at the target site. The remaining tissue is then removed with a sponge or similar material. The voltage generally must be low enough to prevent charring and potential scarring of the underlying dermis.

These electrosurgical devices and procedures, however, suffer from a number of disadvantages. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. This cutting effect generally results in the production of smoke, or an electrosurgical plume, which can spread bacterial or viral particles from the tissue to the surgical team or to other portions of the patient's body. In addition, the tissue is parted along the pathway of evaporated cellular fluid, inducing undesirable collateral tissue damage in regions surrounding the target tissue site.

Recently, a new less invasive procedure for treating skin has been developed, termed Micro-Dermabrasion. This procedure involves delivering fine crystal grains, typically corundum or aluminum oxide, through a handpiece onto the skin's surface, where the crystal grains remove dead and damaged skin cells and help to stimulate the growth of new collagen in the underlying skin. The crystal grains remove only the top superficial layer of dead skin cells, the stratum corneum, without causing significant damage to the underlying epidermis layer. The procedure has been used for treating demarcation lines and wrinkles, photo-damaged skin, acne, pigmentation, scarring, sun damaged skin and cancerous lesions.

While the early marketing studies of the Micro-Dermabrasion process have been promising, this new technology still has a number of shortcomings. For one thing, the crystal grains are difficult to remove once they are embedded into the skin, which has generated some health concerns. In addition, these crystals may often get into the patient's airways or eyes, causing sneezing or other discomfort during the procedure. Moreover, the crystals may scratch the skin or cause minor scarring or discoloration on the neck or darker skins. Finally, since this procedure does not involve the application of heat, it may not have any effect on the underlying collagen in the epidermis and the dermis. Thus, it may not reduce the underlying wrinkles or stimulate any new collagen growth, as claimed in the early marketing studies of this process.

SUMMARY OF THE INVENTION

The present invention provides systems, apparatus and methods for selectively applying electrical energy to structures on the external surface of a patient's body. The systems and methods of the present invention are particularly useful in dermatological procedures, i.e., surface treatment of the patient's outer skin, such as the epidermis and/or the stratum corneum layer.

In one aspect of the invention, a method includes positioning an active electrode adjacent to or near a target site on a patient's outer skin, and applying a sufficient high frequency voltage to the active electrode to remove the stratum corneum without removing the entire epidermis layer. In this manner, the present invention removes dead and/or damaged skin cells on the surface of the skin which improves the overall appearance of the skin. In addition, this process helps to stimulate the bodies own rejuvenation process. In some embodiments, this rejuvenation process occurs by the actual removal of the stratum corneum, which accelerates the regrowth of new cell layers in the skin. In other embodiments, thermal energy is applied to the underlying epidermis and/or dermis to stimulate the growth of new collagen. In both of these embodiments, the skin appears healthier and, in some cases, small wrinkles are removed or reduced.

In a specific configuration, a return electrode is positioned in the region of the target site and electrically conductive fluid is delivered or applied to the target site such that an electrically conductive path is formed between the active and return electrodes through the conductive fluid. The conductive fluid may be delivered to the target site through the electrosurgical probe, through a separate instrument, or it may be applied directly to the target site or to the electrodes (e.g., a conductive gel or a viscous liquid). In any of these embodiments, the conductive fluid provides a conductive path for the electric current to thereby limit or completely avoid current flow into the tissue. In the exemplary embodiment, the return electrode is located on the electrosurgical probe spaced proximally from the active electrode, and the conductive fluid is delivered through or along the shaft of the probe.

In another aspect of the invention, a layer of skin is ablated at relatively low temperatures to minimize collateral damage, and, in some cases, to allow the procedure to be performed without administering anesthesia to the patient. In one embodiment, an active electrode is positioned adjacent to or near the target site on a patient's skin, and sufficient high frequency voltage is applied to the active electrode to ablate an outer layer of tissue at the target site while maintaining a temperature of the exposed surface of the underlying layer less than about 50° C., preferably less than about 40° C.

In the exemplary embodiments, the stratum corneum tissue is ablated with molecular dissociation or disintegration processes. Conventional electrosurgery cuts through tissue by rapidly heating the tissue until cellular fluids explode, producing a cutting effect along the pathway of localized heating. The present invention volumetrically removes the tissue in a cool ablation process that minimizes thermal damage to surrounding tissue. In these processes, the high frequency voltage applied to the active electrode(s) is sufficient to vaporize the electrically conductive fluid (e.g., gel or saline) between the electrode(s) and the tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 50 microns with minimal heating of, or damage to, surrounding or underlying tissue structures. A more complete description of this phenomena is described in commonly assigned U.S. Pat. No. 5,697,882, the complete disclosure of which is incorporated herein by reference.

In some embodiments, the tissue is removed or ablated by directly contacting the target tissue with the active electrode or the plasma. In other embodiments, the active electrode(s) are spaced from the tissue a sufficient distance to minimize or avoid contact between the tissue and the plasma formed around the active electrode(s). Typically, the active electrode(s) are spaced a distance of at least 0.5 mm, usually at least about 1.0 mm, and often about 2.0 mm from the target site. Applicant believes that the electrons that carry the electrical current are hotter than the ions within the plasma. In these embodiments, contact between the heated electrons in the plasma and the tissue is minimized as these electrons travel from the plasma back through the conductive fluid to the return electrode. The ions within the plasma will have sufficient energy, however, under certain conditions such as higher voltages, to accelerate beyond the plasma to the tissue. Thus, the electrons, which are carried away from the target tissue, carry most of the thermal byproducts of the plasma with them, allowing the ions to break apart the tissue molecules in a substantially non-thermal manner.

In another aspect of the invention, it is desired to apply a selected amount of thermal energy to the epidermis or the dermis in order to stimulate the growth of new collagen with the patient's skin. In these embodiments, the active electrode(s) may be brought closer to the patient's skin, or the voltage levels applied to the electrodes may be increased. Alternatively, an active electrode having higher current densities (e.g., electrodes with sharp edges or asperities) may be used, or an electrically conductive gel may be applied to the target site. In the latter embodiment, applicant has found that the gel will retain heat on the surface of the skin, which will result in a greater amount of thermal energy being applied to the skin without ablating the skin beyond the desired level, i.e., the stratum corneum.

In another embodiment, the method further includes the step of vaporizing the electrically conductive fluid near the active electrode into a plasma at relatively low temperatures, preferably lower than about 100° C., more preferably lower than about 80° C. The lower temperature of the conductive fluid will further reduce any risk of undesired thermal damage to tissue surrounding the target site and provide an even more precise tissue removal. In one aspect of the invention, the electrically conductive fluid itself has a relative low vaporization temperature (e.g., preferably below about 100° C. or below 80° C.) at atmospheric pressure. In other embodiments, the electrically conductive fluid is cooled to temperatures less than about 30° C., usually less than 10° C., prior to delivery of this fluid to the target site.

Apparatus according to the present invention generally include an electrosurgical instrument having a shaft with proximal and distal ends, and an electrode assembly at the distal end of the shaft. The electrode assembly comprises one or more active electrode(s) spaced from one or more return electrode(s). A power supply is coupled to the electrode assembly for applying a sufficient high frequency voltage difference between the active and return electrodes to remove the stratum corneum layer of the patient's outer skin without removing the entire epidermis layer.

In a specific configuration, the apparatus includes a supply of electrically conductive fluid and a fluid delivery element for delivering electrically conducting fluid to the electrode terminal(s) and the target site. The fluid delivery element may be located on the instrument, e.g., a fluid lumen or tube, or it may be part of a separate instrument. Alternatively, an electrically conducting gel or spray, such as a saline electrolyte or other conductive gel, may be applied to the target site. In this embodiment, the apparatus may not have a fluid delivery element. In both embodiments, the electrically conducting fluid will preferably generate a current flow path between the active electrode(s) and one or more return electrode(s). In an exemplary embodiment, the return electrode is located on the instrument and spaced a sufficient distance from the active electrode(s) to substantially avoid or minimize current shorting therebetween and to shield the return electrode from tissue at the target site.

The electrosurgical instrument will preferably include an electrically insulating electrode support member, preferably an inorganic support material (e.g., ceramic, glass, glass/ceramic, etc.) having a tissue treatment surface at the distal end of the instrument shaft. One or more electrode terminal(s) are coupled to, or integral with, the electrode support member such that the electrode terminal(s) are spaced from the return electrode. In a specific configuration, the electrosurgical instrument includes an insulating member around the active electrode(s) that forms a plasma chamber adjacent to the active electrode(s). The insulating member preferably comprises an inorganic material, such as ceramic or glass, and it may comprise a transparent material that allows the physician to view the plasma formed therein. In some embodiments, the return electrode(s) are positioned exterior to the plasma chamber, proximally spaced on the instrument as described above. In other embodiments, the return electrode(s) may be positioned within the insulating member such that the electric currents are completely confined to the plasma chamber. In one configuration, the instrument further include a fluid lumen for delivering electrically conductive fluid to the plasma chamber, and a second fluid lumen for aspirating excess conductive fluid from the plasma chamber. The fluid lumens create a fluid recirculation system for minimizing the amount of conductive fluid that leaks onto the patient and for reducing the temperature of the conductive fluid in and around the plasma chamber.

In an exemplary embodiment, the electrosurgical instrument comprises a disposable tip having an electrode assembly coupled to a moldable inorganic insulating member, such as silicone. In this embodiment, the insulating member is molded into a shape to accommodate the active and return electrodes to form a compact, inexpensive disposable electrode assembly that may be attached to a handle or shaft of the instrument. In a specific configuration, the active electrode comprises a loop electrode located within the insulating member and spaced about 0.2 to 1.0 mm from the distal edge of the insulating member to provide spacing between the active electrode and the tissue. The disposable tip further includes a fluid lumen having an opening near the distal edge of the insulating member to allow delivery of electrically conductive fluid to the target site.

A further understanding of the nature and advantages of the invention will become apparent by reference to the remaining portions of the specification and drawings.

BRIEF DESCRIPTION OF THE DRAWINGS

FIGS. 9A-13 are side views of the individual wafer layers of the electrode support;

FIGS. 9B-12B are cross-sectional views of the individual wafer layers;

DESCRIPTION OF SPECIFIC EMBODIMENTS

Figure 1:
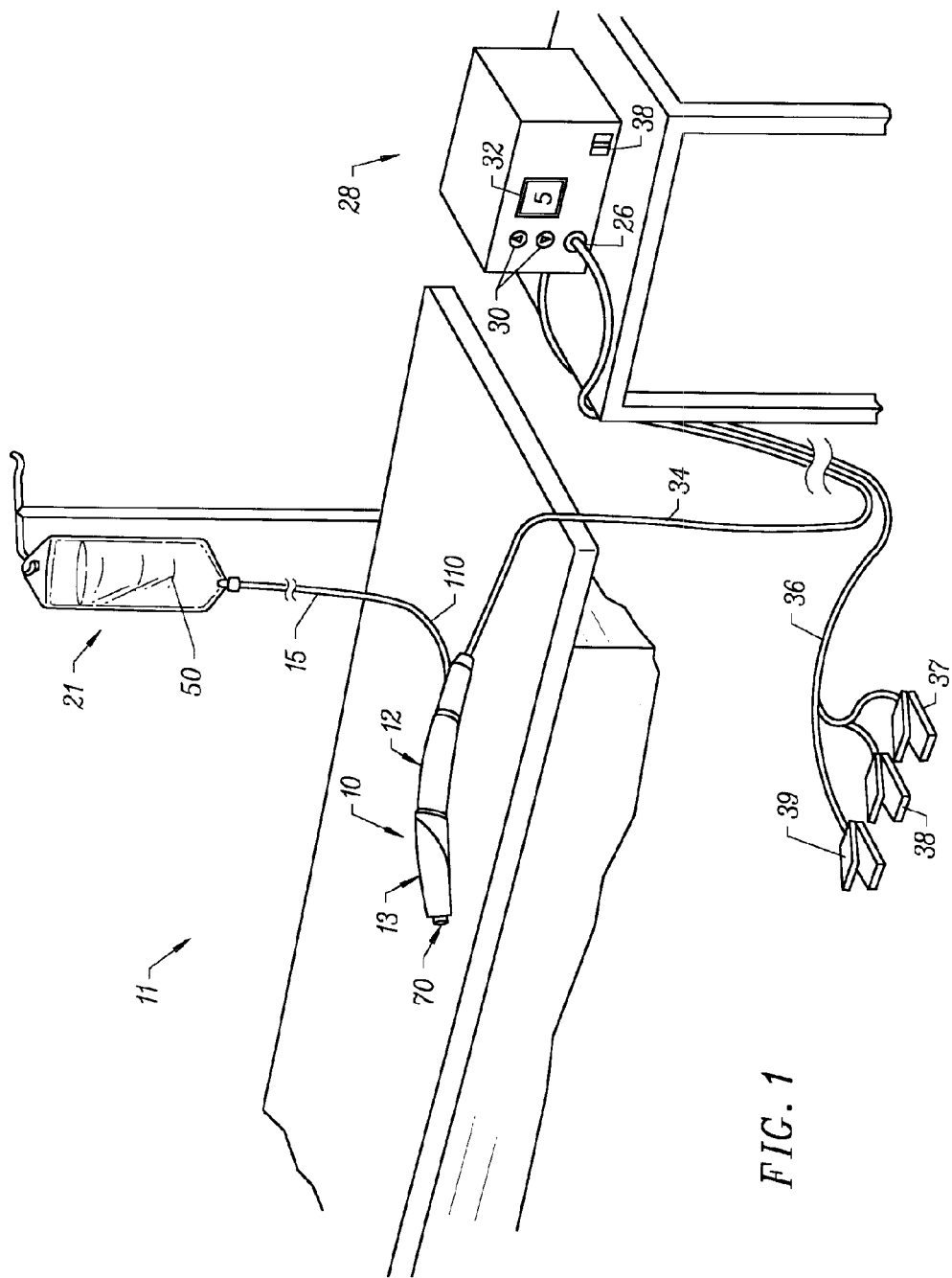
FIG. 1 is a perspective view of an electrosurgical system for treating a patient's skin including an electrosurgical generator and an electrosurgical probe or handpiece.

The present invention provides systems and methods for selectively applying electrical energy to a target location within or on a patient's body, particularly including procedures on an external body surface, such as collagenous tissue within the eye and epidermal and dermal tissues in the skin. For convenience, the remaining disclosure will be directed specifically to skin tissue removal and/or the stimulation of collagen growth in the epidermis or dermis, e.g., the removal of the stratum corneum layer. However, it will be appreciated that the system and method can be applied equally well to procedures involving other tissues of the body, as well as to other procedures including open procedures, intravascular procedures, interventional cardiology procedures, urology, laparascopy, arthroscopy, thoracoscopy or other cardiac procedures, cosmetic surgery, orthopedics, gynecology, otorhinolaryngology, spinal and neurologic procedures, oncology and the like.

The present invention applies high frequency (RF) electrical energy to one or more active electrodes adjacent an external body surface, such as the outer surface of the skin, to remove and/or modify the structure of tissue structures within the skin. Depending on the specific procedure, the present invention may be used to: (1) ablate the outer stratum corneum layer with minimal thermal energy applied to the underlying epidermis and dermis layers; (2) ablate the outer stratum corneum layer with a sufficient amount of thermal energy applied to the underlying skin to stimulate the growth of new collagen; or (3) heat the outer stratum corneum layer sufficiently to remove this layer without causing collateral damage to the underlying epidermis.

In one method of the present invention, a high frequency voltage difference is applied between one or more active electrode(s) and one or more return electrode(s) to develop high electric field intensities in the vicinity of the target tissue. The high electric field intensities adjacent the electrode terminal(s) lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a liquid or gas, such as isotonic saline or blood, delivered to the target site, or a viscous fluid, such as a gel, applied to the target site. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under the conditions described herein, induces the discharge of energetic electrons and photons from the vapor layer and to the surface of the target tissue. This energy may be in the form of energetic photons (e.g., ultraviolet radiation), energetic particles (e.g., electrons or ions) or a combination thereof. A more detailed description of this phenomena, termed Coblation™ can be found in commonly assigned U.S. Pat. No. 5,697,882 the complete disclosure of which is incorporated herein by reference.

Applicant believes that the principle mechanism of tissue removal in the Coblation™ mechanism of the present invention is energetic electrons or ions that have been energized in a plasma adjacent to the electrode terminal(s). When a liquid is heated enough that atoms vaporize off the surface faster than they recondense, a gas is formed. When the gas is heated enough that the atoms collide with each other and knock their electrons off in the process, an ionized gas or plasma is formed (the so-called "fourth state of matter"). A more complete description of plasma can be found in Plasma Physics, by R. J. Goldston and P. H. Rutherford of the Plasma Physics Laboratory of Princeton University (1995). When the density of the vapor layer (or within a bubble formed in the electrically conducting liquid) becomes sufficiently low (i.e., less than approximately 1020 atoms/cm3 for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating a small of gas and ionizing the gas by driving an electric current through it, or by shining radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

In the above procedure, it may also be desirable to stimulate the growth of collage in the tissue layers underlying the removed or ablated epidermal tissue. In these procedures, the temperature of the electrode terminal(s) can be carefully controlled such that sufficient thermal energy is transferred to these underlying layers to contract, damage or otherwise injure these layers such that the body regrows collagen in this region. The thermal energy may be transferred directly through RF current that passes through and resistively heats the underlying tissue layers, or it may be transferred indirectly by heating the electrically conducting fluid, and allowing the heated fluid to contact the underlying layers after the epidermal layers have been removed. Collagen growth within the skin typically occurs after the area has been heated to temperatures in the range of about 40° C. to about 65° C. The preferred depth of heating to effect the stimulation of collagen growth in the heated region (i.e., the depth to which the tissue is elevated to temperatures between 40° C. to 65° C.) generally depends on the thickness and location of the tissue. The depth of heating is usually in the range from 0.1 mm to 0.5 mm.

The present invention is also useful for removing tissue around nerves, such as cranial nerves, e.g., facial nerves, vestibulocochlear nerves and the like. One of the significant drawbacks with the prior art RF devices and lasers is that these devices do not differentiate between the target tissue and the surrounding nerves or bone. Therefore, the surgeon must be extremely careful during these procedures to avoid damage to the nerves within and around the target site. In the present invention, the Coblation™ process for removing tissue results in extremely small depths of collateral tissue damage as discussed above. This allows the surgeon to remove or cut tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more electrode terminal(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In addition to the above, applicant has discovered that the Coblation™ mechanism of the present invention can be manipulated to ablate or cut certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break. Accordingly, the present invention in its current configuration generally does not ablate or remove such fatty tissue. Of course, factors may be changed such that these double bonds can also be broken in a similar fashion as the single bonds (e.g., increasing voltage or changing the electrode configuration to increase the current density at the electrode tips). A more complete description of this phenomena can be found in co-pending U.S. patent application Ser. No. 09/032,375, filed Feb. 27, 1998, the complete disclosure of which is incorporated herein by reference.

The present invention also provides systems, apparatus and methods for selectively removing tumors, e.g., facial tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the electrode terminal(s) and one or more return electrode(s) to volumetrically remove at least a portion of the tissue cells in the tumor through the dissociation or disintegration of organic molecules into non-viable atoms and molecules. Specifically, the present invention converts the solid tissue cells into non-condensable gases that are no longer intact or viable, and thus, not capable of spreading viable tumor particles to other portions of the patient's body or to the surgical staff. The high frequency voltage is preferably selected to effect controlled removal of these tissue cells while minimizing substantial tissue necrosis to surrounding or underlying tissue. A more complete description of this phenomena can be found in co-pending U.S. patent application Ser. No. 09/109,219, filed Jun. 30, 1998, the complete disclosure of which is incorporated herein by reference.

The electrosurgical instrument of the present invention comprises a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. For cosmetic surgery or dermatology procedures, the shaft will have any suitable length and diameter that would facilitate handling by the surgeon.

The electrode terminal(s) are preferably supported within or by an inorganic insulating support positioned near the distal end of the instrument shaft. The inorganic insulating support will typically comprise a material selected from the group of ceramic, glass, silicone or the like. The return electrode may be located on the instrument shaft, on another instrument, or on the external surface of the patient (i.e., a dispersive pad). In most applications, applicant has found that it is preferably to have the return electrode on or near the shaft of the instrument to confine the electric currents to the target site. In some applications and under certain conditions, however, the invention may be practiced in a monopolar mode, with the return electrode attached to the external surface of the patient. The proximal end of the instrument will include the appropriate electrical connections for coupling the return electrode(s) and the active electrode(s) to a high frequency power supply, such as an electrosurgical generator.

The current flow path between the active electrodes and the return electrode(s) may be generated by submerging the tissue site or the electrode assembly in an electrical conducting fluid (e.g., within a viscous fluid, such as an electrically conductive gel) or by directing an electrically conducting fluid along a fluid path to the target site (i.e., a liquid, such as isotonic saline, hypotonic saline or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood or inner cellular fluids, may be sufficient to establish a conductive path between the return electrode(s) and the active electrode(s), and to provide the conditions for establishing a vapor layer, as described above. However, conductive fluid that is introduced to the target site is generally preferred over bodily floods, such as blood, because these fluids will tend to coagulate at certain temperatures. In addition, the patient's bodily fluids may not have sufficient electrical conductivity or ionic strength to adequately form a plasma in some applications. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the active electrode(s) when there is insufficient conductive fluid around the active electrode(s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998, the complete disclosure of which is incorporated herein by reference.

In some procedures, it may also be necessary to retrieve or aspirate the electrically conductive fluid and/or the non-condensible gaseous products of ablation. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. A more complete description of instruments incorporating aspiration electrode(s) can be found in commonly assigned, co-pending patent application entitled "Systems And Methods For Tissue Resection, Ablation And Aspiration", filed Jan. 21, 1998, the complete disclosure of which is incorporated herein by reference.

The present invention may use a single active electrode or an electrode array distributed over a contact surface of a probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode may be a tubular member of conductive material proximal to the electrode array at the tip which also serves as a conduit for the supply of the electrically conducting fluid between the active and return electrodes. The application of high frequency voltage between the return electrode and the electrode array results in the generation of high electric field intensities at the distal tips of the electrode terminals with conduction of high frequency current from each individual electrode terminal to the return electrode. The current flow from each individual electrode terminal to the return electrode is controlled by either active or passive means, or a combination thereof, to deliver electrical energy to the surrounding conductive fluid while minimizing energy delivery to surrounding (non-target) tissue.

The application of a high frequency voltage between the return electrode and the electrode array for appropriate time intervals effects heating of the conductive fluid and contraction of the target tissue. In some embodiments, the tissue volume over which energy is dissipated (i.e., a high current density exists) may be precisely controlled, for example, by the use of a multiplicity of small electrode terminals whose effective diameters or principal dimensions range from about 10 mm to 0.01 mm. The use of small diameter electrode terminals increases the electric field intensity and reduces the extent or depth of tissue heating as a consequence of the divergence of current flux lines which emanate from the exposed surface of each electrode terminal.

In other embodiments, the active electrode(s) will have an active portion or surface with surface geometries shaped to promote the electric field intensity and associated current density along the leading edges of the electrodes. Suitable surface geometries may be obtained by creating electrode shapes that include preferential sharp edges (e.g., loops), or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes.

Additionally or alternatively, the active electrode surface(s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a PH less than 7.0 or by using a high velocity stream of abrasive particles (e.g., grit blasting) to create asperities on the surface of an elongated electrode.

Additionally or alternatively, the active electrode surface(s) may be provided by assembling alternating layers of electrically conductive members (i.e., electrodes) and electrically insulating spacers. By way of example, an active electrode having multiple circular edges may be constructed using alternating layers of concentric, thin metal washers (e.g., titanium, stainless steel or the like), having outside diameters D. The washers may be separated by thin concentric insulating spacers (e.g., anodized aluminum, ceramic, glass, glass ceramic, plastic, etc.) having an outside diameter D' which is less than D so that the edges of the metal washers extend beyond the insulating spacers. The electrode assembly can be constructed by placing the metal washers over a central, electrically conductive mandrel, which provides for electrical communication between the power source and the multiple metal "washer" shaped electrodes. In this arrangement, the electrodes are preferably at the same source polarity since they are in contact with a common electrical lead (i.e., mandrel).

The active electrode(s) are formed over a tissue treatment surface on the shaft of the electrosurgical probe. The return electrode surface will be recessed relative to the distal end of the probe and may be recessed within a fluid conduit provided for the introduction of electrically conducting fluid to the site of the target tissue and electrode terminal(s).

The area of the tissue treatment surface can vary widely, and the tissue treatment surface can assume a variety of geometries, with particular areas and geometries being selected for specific applications. Active electrode surfaces can have areas in the range from $0.25$ mm$^2$ to $75$ mm$^2$, usually being from about $0.5$ mm$^2$ to $40$ mm$^2$. The geometries can be loop, planar, concave, convex, hemispherical, conical, linear "in-line" array or virtually any other regular or irregular shape. Alternatively or additionally, the active electrode(s) may be formed on lateral surfaces of the electrosurgical probe shaft (e.g., in the manner of a spatula), facilitating access to certain body structures in endoscopic procedures.

In the representative embodiment, the active electrode comprises a loop electrode having two ends coupled to a contact surface of the electrode support member so that the loop extends distally from the contact surface. The loop electrode will typically extend about 0.01 to 2.0 mm from the contact surface of the support member, and will have a length slightly less than the width of the support member, or about 1 to 40 mm, usually about 5 to 20 mm. In the exemplary embodiment, the electrode support comprises a silicone material of about 40 to 100 shore A°.

In other embodiments, the electrode support comprises a plurality of wafer layers bonded together, e.g., by a glass adhesive or the like. The wafer layers each have conductive strips printed thereon to form the electrode terminal(s) and the return electrode(s). In one embodiment, the proximal end of the wafer layers will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode will preferably comprise a metallic material, such as gold, platinum, palladium, tungsten, silver or the like. Suitable multilayer ceramic electrodes are commercially available from e.g., VisPro Corporation of Beaverton, Oreg.

The electrically conducting fluid should have a threshold conductivity to provide a suitable conductive path between the return electrode and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Alternatively, the fluid may be an electrically conductive gel or spray, such as a saline electrolyte gel, a conductive ECG spray, an electrode conductivity gel, an ultrasound transmission or scanning gel, or the like. Suitable gels or sprays are commercially available from Graham-Field, Inc. of Hauppauge, N.Y. Applicant has found that a more conductive fluid, or one with a higher ionic concentration, will usually provide a more aggressive ablation rate at the same voltage level. This allows for ablation of tissue at lower temperatures. For example, a saline solution with higher levels of sodium chloride than conventional saline (which is on the order of about 0.9% sodium chloride) e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with elements other than sodium, such as potassium, magnesium, calcium and other metals near the left end of the periodic chart. In addition, other electronegative elements may be used in place of chlorine, such as fluorine.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. The electrically conductive fluid also helps maintain the tissue temperature as low as possible during the procedure.

The voltage applied between the return electrode and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts, usually about 150 to 350 volts rms depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts and preferably in the range of 20 to 800 volts and more preferably in the range of about 300 to 700 volts peak to peak (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, the total number of electrode(s) and/or the maximum allowed temperature selected for the probe tip. The power source allows the user to select the voltage level according to the specific requirements of a particular arthroscopic surgery, cosmetic surgery, dermatological procedure, ophthalmic procedures, open surgery or other endoscopic surgery procedure. A description of a suitable power source can be found in U.S. patent application Ser. No. 09/058,571, filed on Apr. 10, 1998, the complete disclosure of which has been previously incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the size of the electrode terminal(s), the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

During the surgical procedure, the distal end of the probe or the active electrode(s) may be maintained at a small distance away from the target tissue surface. This small spacing minimizes the thermal energy applied to the tissue, which reduces collateral tissue damage and, in some embodiments, sufficiently reduces the temperature of the tissue to allow for limited or no anesthesia to be used during the procedure. Applicant believes that this spacing minimizes contact between the heated electrons in the plasma layer because these electrons travel back (proximally) from the plasma layer through the conductive media to the return electrode. The ions within the plasma, however, will have sufficient energy under certain conditions to accelerate beyond the plasma layer to the tissue. This allows the physician to ablate the surface layer of tissue while minimizing the thermal energy applied to the underlying tissue layers.

In addition, spacing the distal end of the probe away from the target tissue allows for the continual resupply of electrically conducting fluid into the interface between the electrode terminal(s) and the target tissue surface. This continual resupply of the electrically conducting fluid helps to ensure that the thin vapor layer will remain between electrode terminal(s) and the tissue surface. In addition, dynamic movement of the electrode terminal(s) over the tissue site allows the electrically conducting fluid to cool the tissue underlying and surrounding the target tissue to minimize thermal damage to this surrounding and underlying tissue. To that end, the electrically conducting fluid may be cooled to facilitate this cooling of the tissue. Typically, the active electrode(s) will be about 0.02 to 2 mm from the target tissue and preferably about 0.05 to 1.0 mm during the ablation process. One method of maintaining this space is to translate and/or rotate the probe transversely relative to the tissue, i.e., a light brushing motion, to maintain a thin vaporized layer or region between the active electrode and the tissue. Of course, if coagulation or collagen shrinkage of a deeper region of tissue is necessary (e.g., for sealing a bleeding vessel imbedded within the tissue), it may be desirable to press the electrode terminal(s) against the tissue to effect joulean heating therein.

Referring to FIG. 1, an electrosurgical system 11 generally comprises an electrosurgical handpiece or probe 10 connected to a power supply 28 for providing high frequency voltage to a target site and a fluid source 21 for supplying electrically conducting fluid 50 to probe 10. Probe 10 generally includes a proximal handle 12 and a distal tip 13 having an electrode support member 70 with one or an array of electrode terminals 58 and one or more return electrodes 100, 102 (see FIGS. 2, 4 and 5) disposed on the support member 70. A connecting cable 34 has a connector 26 for electrically coupling the electrodes in probe 10 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 110 of probe 10 for supplying electrically conducting fluid 50 to the distal tip 13 (see FIGS. 16 and 17).

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjusting the energy level applied to electrode terminals 58. In an exemplary embodiment, first foot pedal 37 is used to place the power supply into the "ablation" mode and second foot pedal 38 places power supply 28 into the "coagulation" mode. The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing the vapor layer and accelerating these charged particles against the tissue). As discussed above, the requisite voltage level for ablation will vary depending on the number, size, shape and spacing of the electrodes, the distance in which the electrodes extend from the support member, etc. When the surgeon is using the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 28 applies a low enough voltage to one or more electrode terminals (or one or more coagulation electrodes) to avoid vaporization of the electrically conductive fluid, formation of a plasma and subsequent molecular dissociation of the tissue. The surgeon may automatically toggle the power supply between the ablation and coagulation modes by alternatively stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37.

Figure 22:
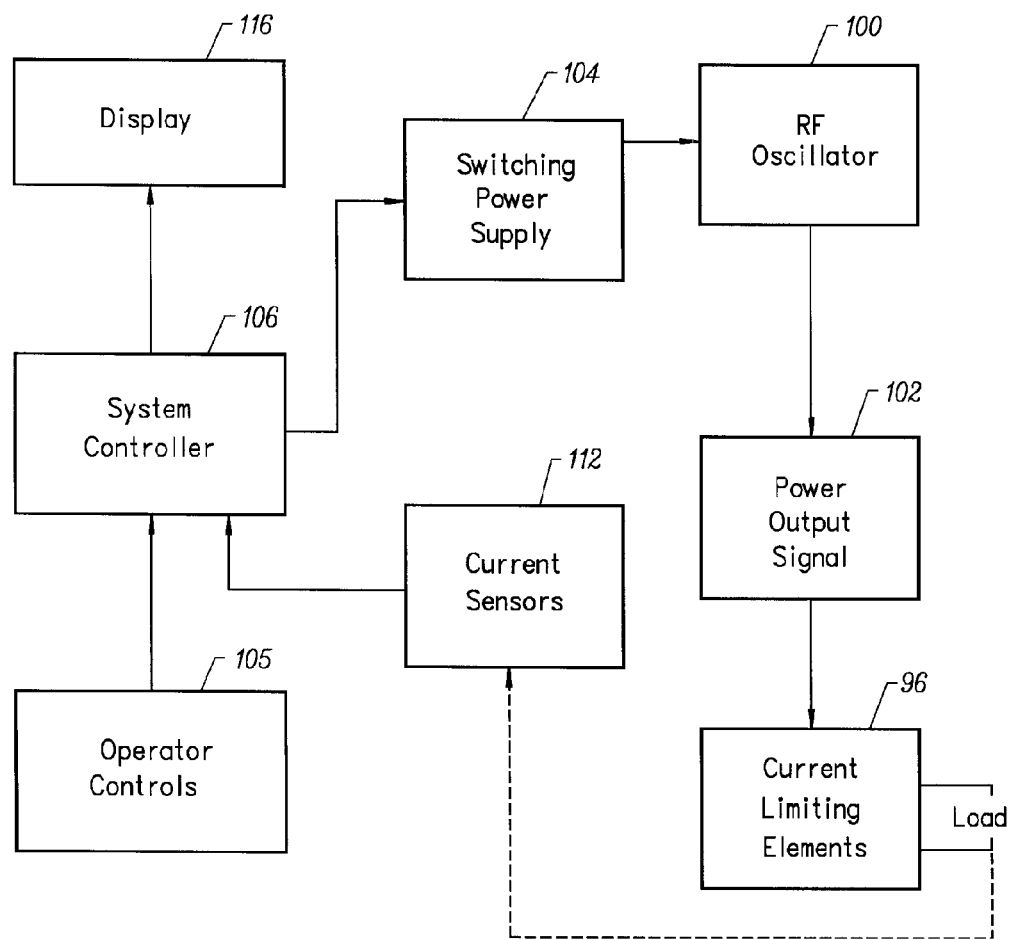
FIG. 22 schematically illustrates one embodiment of a power supply according to the present invention.
Figure 23:
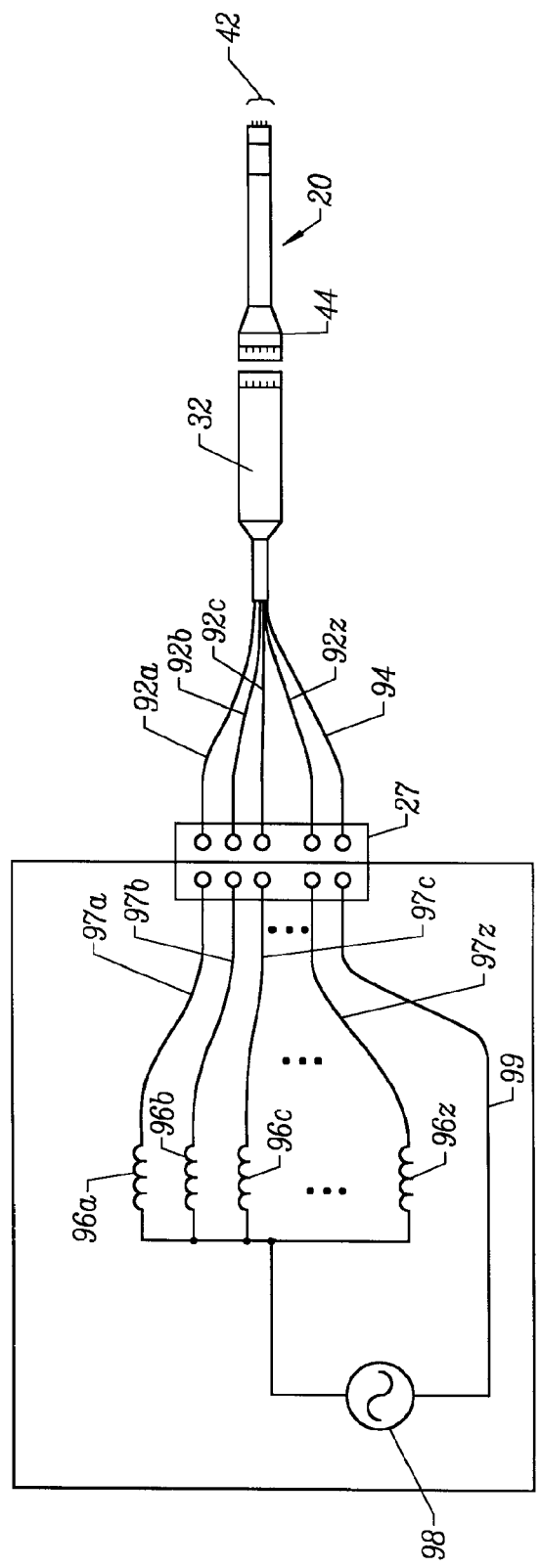
FIG. 23 illustrates an electrosurgical system incorporating a plurality of active electrodes and associated current limiting elements.

Referring now to FIGS. 22 and 23, a representative high frequency power supply for use according to the principles of the present invention will now be described. The high frequency power supply of the present invention is configured to apply a high frequency voltage of about 10 to 500 volts RMS between one or more electrode terminals (and/or coagulation electrode) and one or more return electrodes. In the exemplary embodiment, the power supply applies about 70-350 volts RMS in the ablation mode and about 20 to 90 volts in a subablation mode, preferably 45 to 70 volts in coagulation mode (these values will, of course, vary depending on the probe configuration attached to the power supply and the desired mode of operation).

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular procedure, e.g., arthroscopic surgery, dermatological procedure, ophthalmic procedures, open surgery or other endoscopic surgery procedure.

As shown in FIG. 22, the power supply generally comprises a radio frequency (RF) power oscillator 100 having output connections for coupling via a power output signal 102 to the load impedance, which is represented by the electrode assembly when the electrosurgical probe is in use. In the representative embodiment, the RF oscillator operates at about 100 kHz. The RF oscillator is not limited to this frequency and may operate at frequencies of about 300 kHz to 600 kHz. In particular, for cardiac applications, the RF oscillator will preferably operate in the range of about 400 kHz to about 600 kHz. The RF oscillator will generally supply a square wave signal with a crest factor of about 1 to 2. Of course, this signal may be a sine wave signal or other suitable wave signal depending on the application and other factors, such as the voltage applied, the number and geometry of the electrodes, etc. The power output signal 102 is designed to incur minimal voltage decrease (i.e., sag) under load. This improves the applied voltage to the electrode terminals and the return electrode, which improves the rate of volumetric removal (ablation) of tissue.

Power is supplied to the oscillator 100 by a switching power supply 104 coupled between the power line and the RF oscillator rather than a conventional transformer. The switching power supply 140 allows the generator to achieve high peak power output without the large size and weight of a bulky transformer. The architecture of the switching power supply also has been designed to reduce electromagnetic noise such that U.S. and foreign EMI requirements are met. This architecture comprises a zero voltage switching or crossing, which causes the transistors to turn ON and OFF when the voltage is zero. Therefore, the electromagnetic noise produced by the transistors switching is vastly reduced. In an exemplary embodiment, the switching power supply 104 operates at about 100 kHz.

A controller 106 coupled to the operator controls 105 (i.e., foot pedals and voltage selector) and display 116, is connected to a control input of the switching power supply 104 for adjusting the generator output power by supply voltage variation. The controller 106 may be a microprocessor or an integrated circuit. The power supply may also include one or more current sensors 112 for detecting the output current. The power supply is preferably housed within a metal casing which provides a durable enclosure for the electrical components therein. In addition, the metal casing reduces the electromagnetic noise generated within the power supply because the grounded metal casing functions as a "Faraday shield", thereby shielding the environment from internal sources of electromagnetic noise.

The power supply generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors, resistors, capacitors and the like). The daughter board is coupled to the mother board by a detachable multi-pin connector to allow convenient conversion of the power supply to, e.g., applications requiring a different current limiting circuit design. For arthroscopy, for example, the daughter board preferably comprises a plurality of inductors of about 200 to 400 microhenries, usually about 300 microhenries, for each of the channels supplying current to the electrode terminals.

Alternatively, in one embodiment, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

Figure 4:
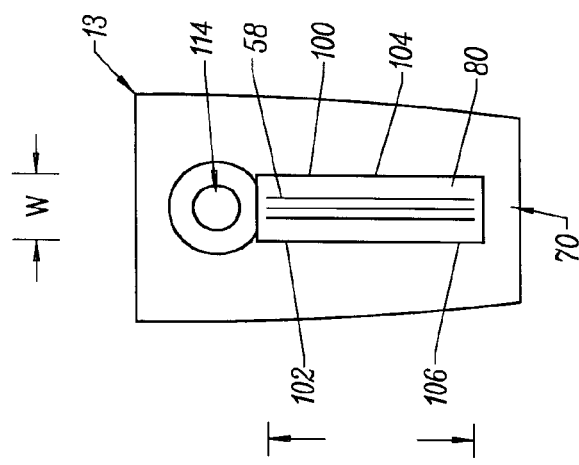
FIG. 4 is an end view of the distal tip of the probe, illustrating an electrode support with a plurality of electrode terminals.
Figure 6:
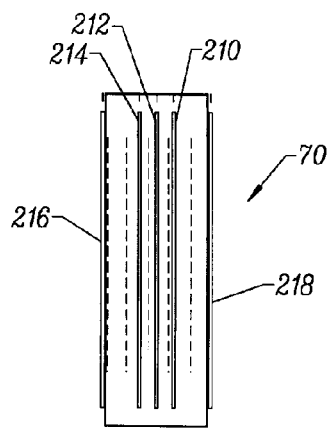
FIG. 6 is an end view of an exemplary electrode support comprising a multi-layer wafer with plated conductors for electrodes.
Figures 7, 8:
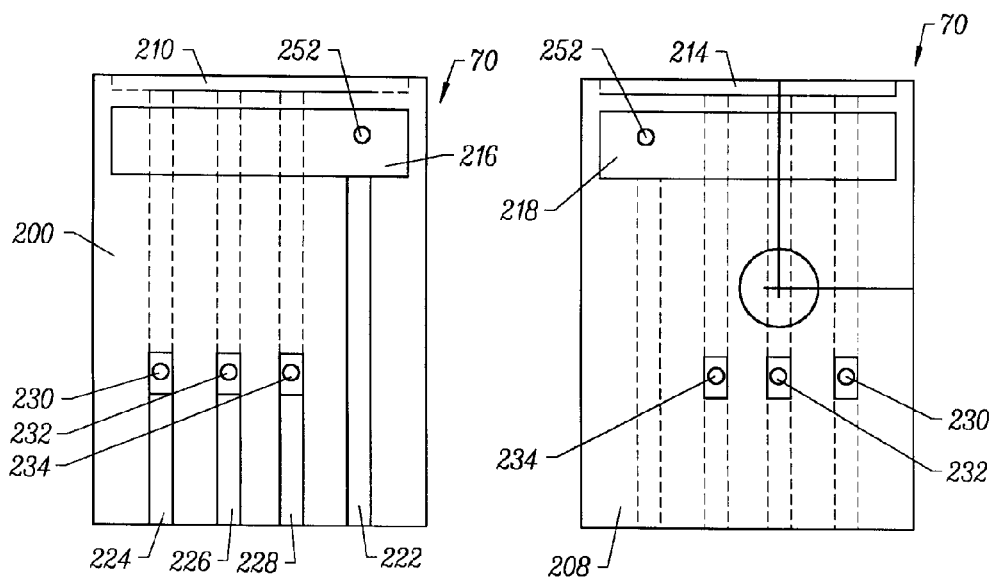
FIGS. 7 and 8 are side views of the electrode support of FIG. 7.

Power output signal may also be coupled to a plurality of current limiting elements 96, which are preferably located on the daughter board since the current limiting elements may vary depending on the application. FIG. 4 illustrates an arrangement that may be used in arthroscopic procedures with a multi-electrode probe. As shown, a high frequency power supply 28 comprises a voltage source 98 which is connected to a multiplicity of current limiting elements 96a, 96b, . . . 96z, typically being inductors having an inductance in the range of about 100 to 5000 microhenries, with the particular value depending on the electrode terminal dimensions, the desired ablation rates, and the like. Capacitors having capacitance values in the range of about 200 to 10,000 picofarads may also be used as the current limiting elements. It would also be possible to use resistors as current limiting elements. The current limiting elements any also be part of a resonant circuit structure, as described in detail in the '909 patent.

Figure 2:
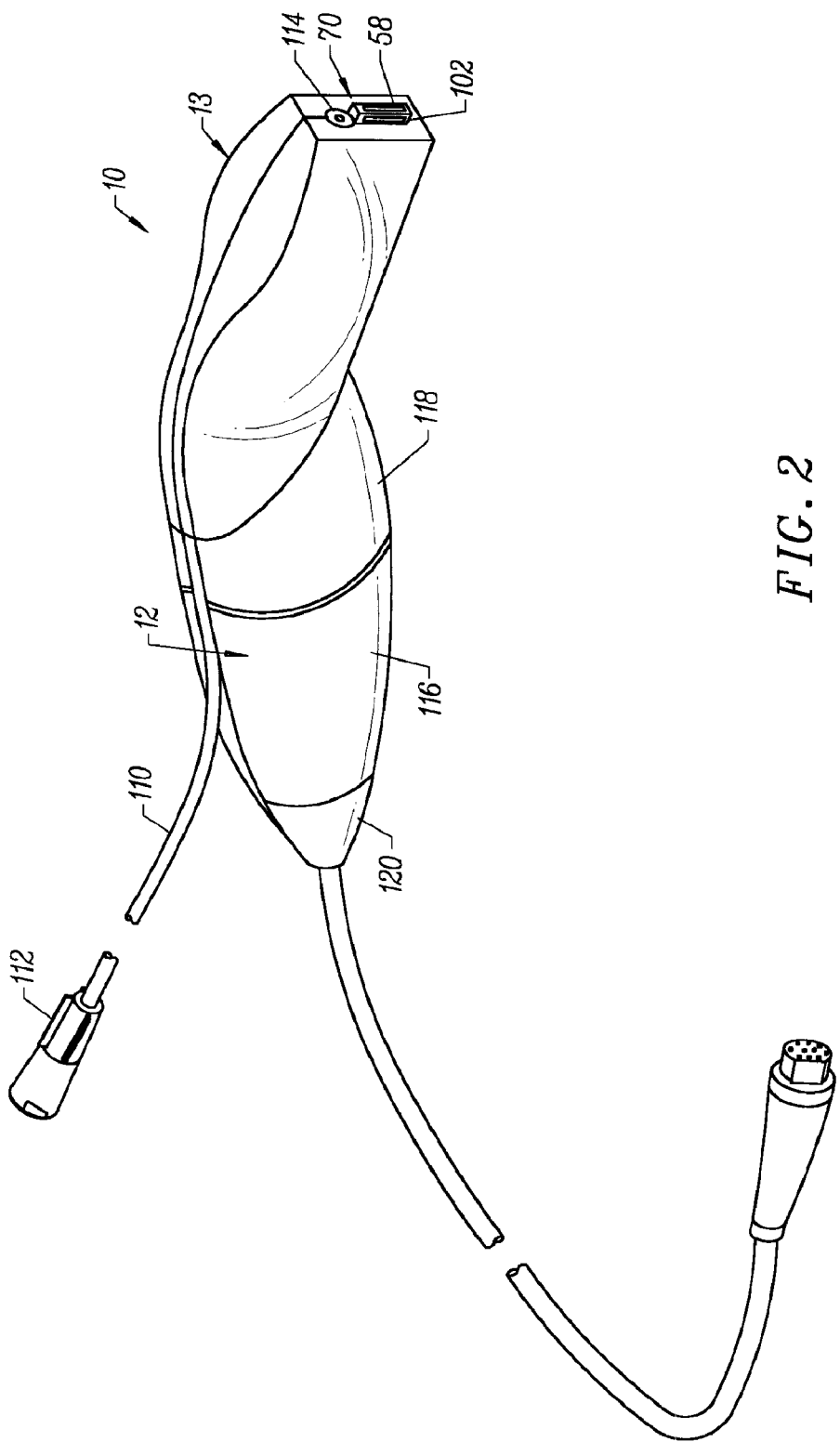
FIG. 2 is a perspective view of one embodiment of an electrosurgical probe constructed according to the principles of the present invention.
Figure 3A:
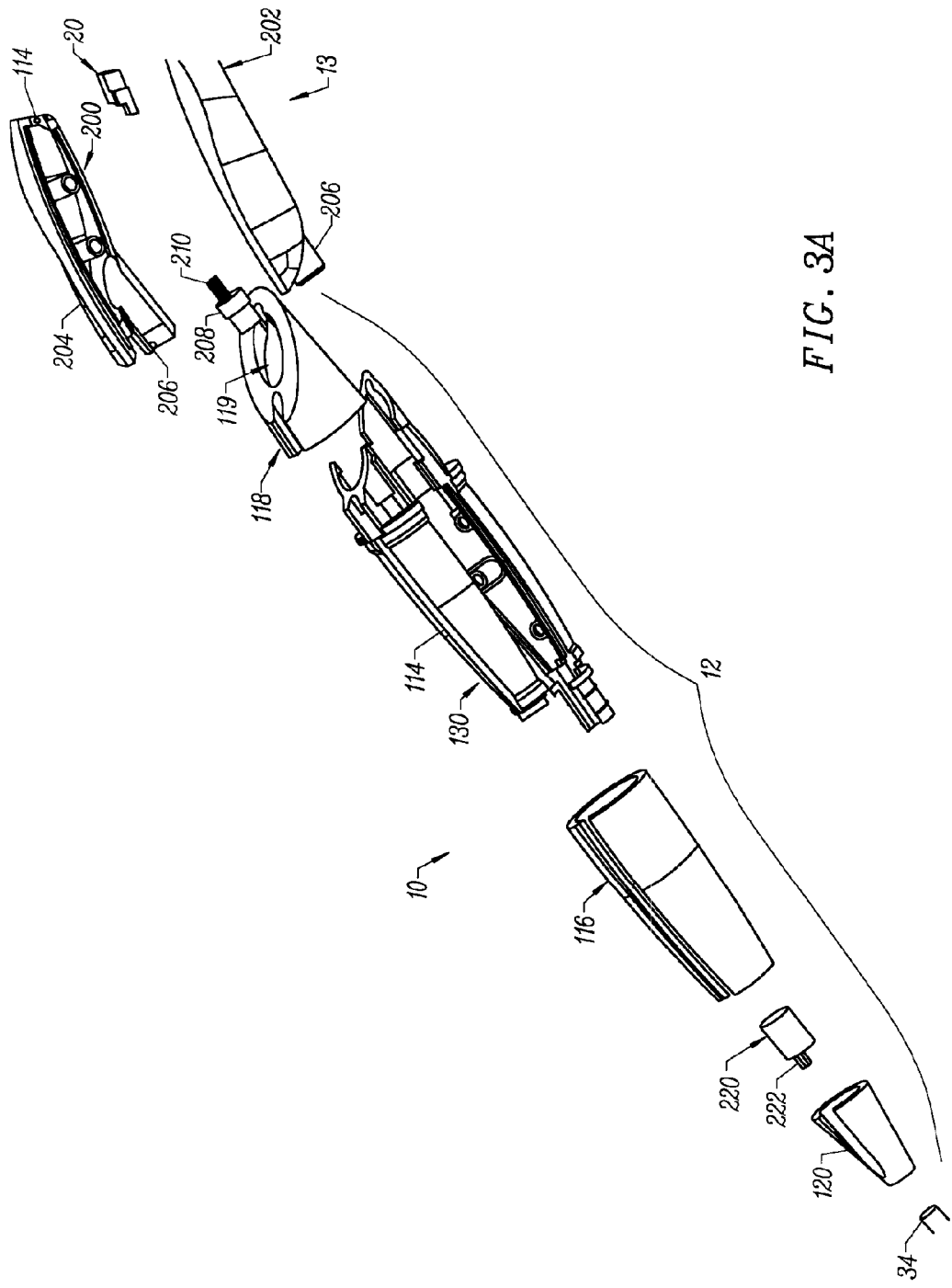
FIGS. 3A-3C are exploded, isometric views of the probe of FIG. 2.
Figure 3B:
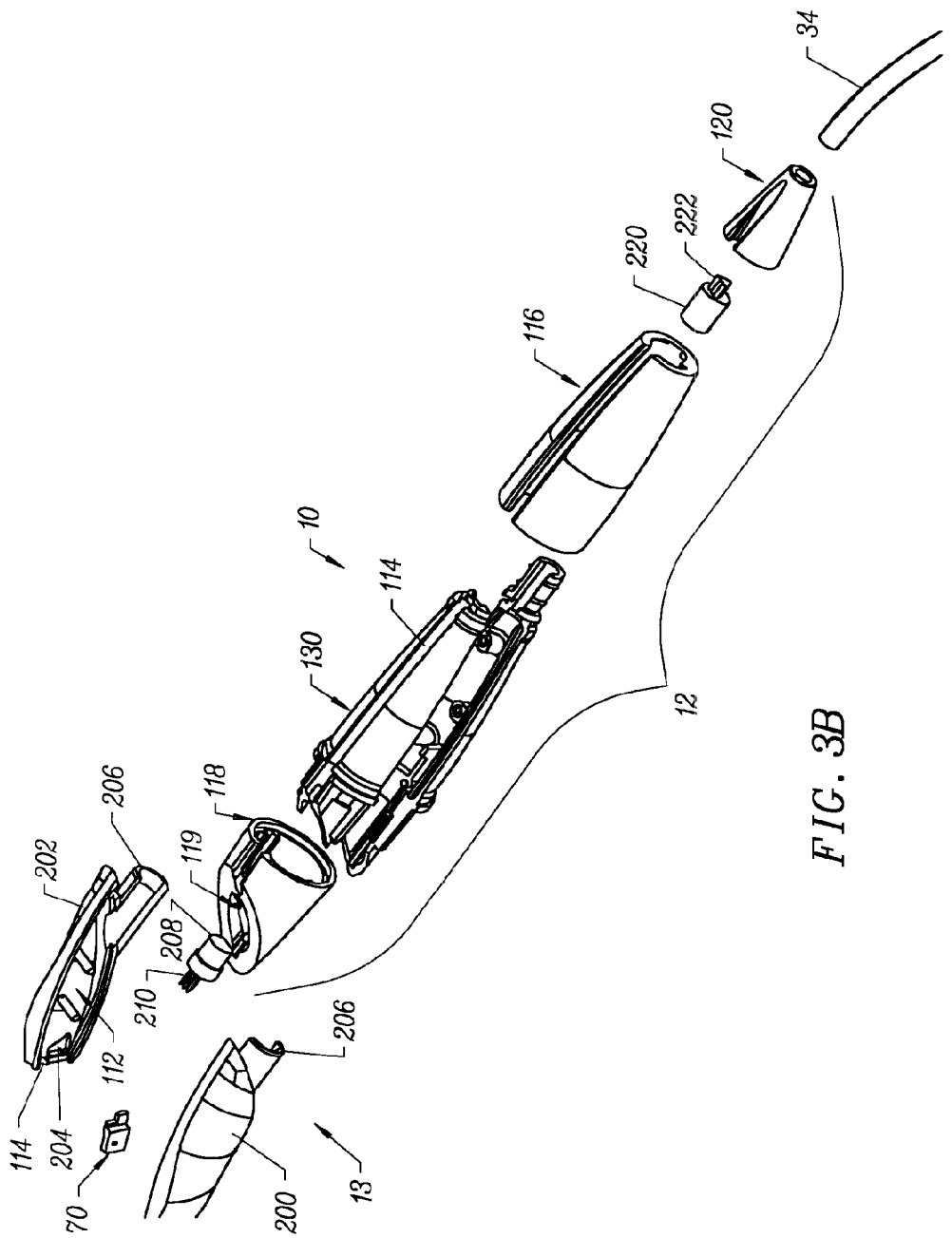
Figure 3C:
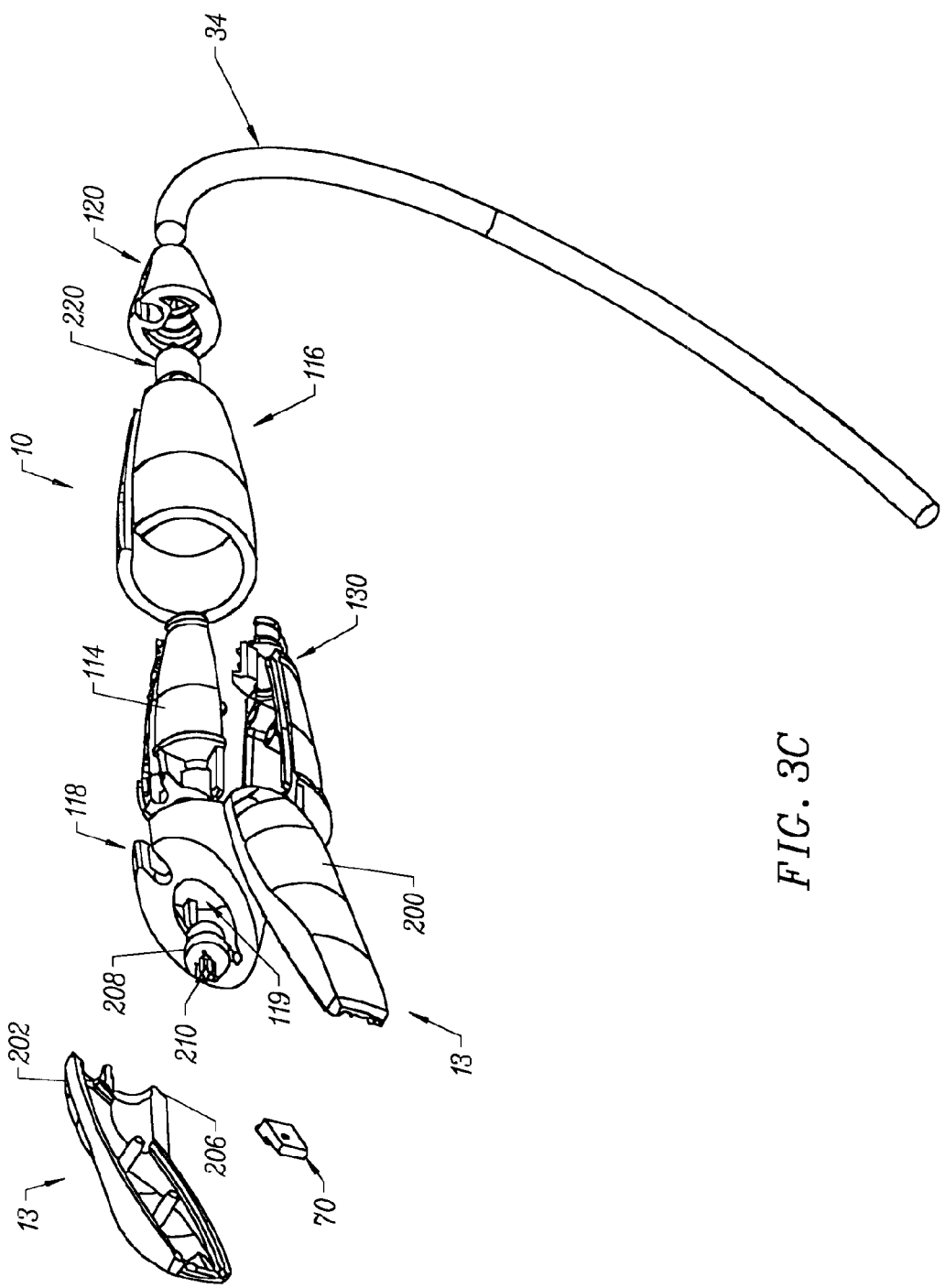
Figure 5:
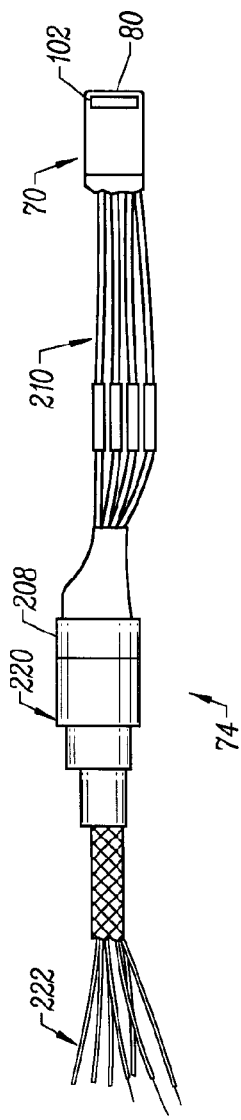
FIG. 5 illustrates the electrical connections and the electrode support of the handpiece in greater detail.

Referring now to FIGS. 2-5, an exemplary electrosurgical probe 10 comprises a shaft or disposable tip 13 removably coupled to a proximal handle 12, and an electrically insulating electrode support member 70 extending from tip 13 for supporting a plurality of electrode terminals 58 (see FIGS. 2 and 5). Tip 13 and handle 12 typically comprise a plastic material that is easily molded into a suitable shape for handling by the surgeon. As shown in FIGS. 3 and 5, handle 12 defines an inner cavity 72 that houses the electrical connections 74 (discussed below in reference to FIG. 5), and provides a suitable interface for connection to electrical connecting cable 34 (see FIG. 1). In the exemplary embodiment, handle 12 is constructed of a steam autoclavable plastic or metal (e.g., polyethylether keytone, or a stable metal alloy containing aluminum and/or zinc) so that it can be re-used by sterilizing handle 12 between surgical procedures. High service temperature materials are preferred, such as a silicone cable jacket and a poly-ether-imide handpiece or ULTEM® that can withstand a repeated exposure to high temperatures.

Referring to FIGS. 4A-4C, tip 13 preferably comprises first and second housing halves 200, 202 that snap fit together, and form a recess 204 therebetween for holding electrode support member 70 within the tip 13. Electrode support member 70 extends from the distal end of tip 13 (usually about 0.5 to 20 mm), and provides support for a plurality of electrically isolated electrode terminals 58 and one or more return electrodes 100, 102 (see FIG. 4). Alternatively, electrode support member 70 may be recessed from the distal end of tip 13 to help confine the electrically conductive fluid around the electrode terminals 58 during the surgical procedure, as discussed above. Electrode support member 70 has a substantially planar tissue treatment surface 80 that is usually disposed at an angle of about 10 to 90 degrees relative to the longitudinal axis of handle 12 to facilitate handling by the surgeon. In the exemplary embodiment, this function is accomplished by orienting tip 13 at an acute angle relative to the longitudinal axis of handle 12.

In the embodiment shown in FIGS. 2-5, probe 10 includes first and second return electrodes 100, 102 for completing the current path between electrode terminals 58 and power supply 28 (see FIG. 1). As shown, return electrodes 100, 102 preferably have fluid contact surfaces on either lateral surface 104, 106 of electrode support member 70 slightly proximal to tissue treatment surface 80, typically about 0.1 to 2 mm, preferably about 0.2 to 1 mm. Return electrodes 100, 102 will usually have an exposed surface area of about 5 mm2 to 25 mm2, preferably about 18 mm2 to about 20 mm2. Return electrodes 100, 102 are coupled to a connector 104 (details of this connection discussed below) that extends to the proximal end of handle 13, where it is suitably connected to power supply 28 (FIG. 1).

Referring to FIGS. 4A-4C and FIG. 5, tip 13 further includes a proximal hub 206 for supporting a male electrical connector 208 that holds a plurality of wires 210 each coupled to one of the electrode terminals 58 and the return electrodes 100, 102 on support member 70 (see FIGS. 7-13 for details of the representative support member 70). A female connector 220 housed within handle 12 is removably coupled to male connector 208, and a plurality of wires 222 extend from female connector 220 through a strain relief 224 to cable 34. Both sets of wires 210, 222 are insulated to prevent shorting in the event of fluid ingress into the probe 10. This design allows for removable connection of the electrodes in tip 13 with the connector 220 within handle 12 so that the handle can be re-used with different tips 13. Probe 10 will preferably also include an identification element, such as a coded resistor (not shown), for programming a particular voltage output range and mode of operation for the power supply. This allows the power supply to be employed with a variety of different probes for a variety of different applications.

As shown in FIG. 5, return electrodes 100, 102 are not directly connected to electrode terminals 58. To complete this current path so that electrode terminals 58 are electrically connected to return electrodes 102, 100, electrically conducting fluid (e.g., isotonic saline or electrically conducting gel) is located between the active and return electrodes during a surgical procedure. In the representative embodiment, probe 10 includes a fluid tube 110 (FIG. 2) for delivering electrically conductive fluid to the target site. Fluid tube 110 is sized to extend through a groove 114 in handle 13 and through an inner cavity 112 (FIG. 3 and FIGS. 4A-4C) in tip 12 to a distal opening 114 (FIG. 4) located adjacent electrode support member 70. Tube 110 extends all the way through inner cavity 112 to opening 114 to eliminate any possible fluid ingress into cavity 112. As shown in FIGS. 1 and 2, fluid tube 110 includes a proximal connector 112 for coupling to an electrically conductive fluid source 21.

Probe 10 will also include a valve or equivalent structure for controlling the flow rate of the electrically conducting fluid to the target site. In the representative embodiment shown in FIGS. 4A-4C, handle 12 comprises a main body 130 coupled between distal hub 118 and strain relief 120, and a rotatable sleeve 116 around main body 130. Distal hub 118 has an opening 119 for receiving proximal hub 206 of tip 13 for removably coupling the tip 13 to the handle 12. Sleeve 116 is rotatably coupled to strain relief 120 and distal hub 118 to provide a valve structure for fluid tube 110. As shown in FIG. 2, fluid tube 110 extends through groove 114 from strain relief 120, through main body 130 and distal hub 120 to tip 13. Rotation of sleeve 116 will impede, and eventually obstruct, the flow of fluid through tube 110. Of course, this fluid control may be provided by a variety of other input and valve devices, such as switches, buttons, etc.

In alternative embodiments, the fluid path may be directly formed in probe 10 by, for example, a central inner lumen or an annular gap (not shown) within the handle and the tip. This inner lumen may be formed near the perimeter of the probe 10 such that the electrically conducting fluid tends to flow radially inward towards the target site, or it may be formed towards the center of probe 10 so that the fluid flows radially outward. In addition, the electrically conducting fluid may be delivered from a fluid delivery element (not shown) that is separate from probe 10. In arthroscopic surgery, for example, the body cavity will be flooded with isotonic saline and the probe 10 will be introduced into this flooded cavity. Electrically conducting fluid will be continually resupplied to maintain the conduction path between return electrodes 100, 102 and electrode terminals 58. A more complete description of alternative electrosurgical probes incorporating one or more fluid lumen(s) can be found in commonly assigned, co-pending application Ser. No. 08/485,219, filed on Jun. 7, 1995, the complete disclosure of which has previously been incorporated herein by reference.

Referring to FIGS. 4 and 5, electrically isolated electrode terminals 58 are spaced apart over tissue treatment surface 80 of electrode support member 70. In the representative embodiment, the tissue treatment surface 80 has a rectangular cross-sectional shape with a length L in the range of about 0.5 mm to 20 mm (preferably about 2 to 10 mm) and a width W in the range from 0.3 mm to 10 mm (preferably about 0.5 to 4 mm). The individual electrode terminals 58 have the dimensions described above, and are preferably substantially flush with tissue treatment surface 80. Applicant has found that this configuration minimizes any sharp electrode edges and/or corners that would promote excessively high electric field intensities and associated current densities when a high frequency voltage is applied to the electrode terminals, thereby minimizing the rate of ablation as preferred for removing thin layers of tissue (e.g., epidermal layers).

It should be noted that the electrode terminals 58 may protrude slightly outward from surface 80, typically by a distance from 0 mm to 2 mm, or the terminals may be recessed from this surface. For example, the electrode terminals 58 may be recessed by a distance from 0.01 mm to 1 mm, preferably 0.01 mm to 0.2 mm. In one embodiment of the invention, the electrode terminals are axially adjustable relative to the tissue treatment surface so that the surgeon can adjust the distance between the surface and the electrode terminals.

Referring now to FIGS. 7-13, an exemplary electrode support member 70 will be described in detail. As shown, electrode support member 70 preferably comprises a multilayer substrate comprising a suitable high temperature, electrically insulating material, such as ceramic. The multilayer substrate is a thin or thick-film hybrid having conductive strips that are adhered to the ceramic wafer layers (e.g., thick-film printed and fired onto or plated onto the ceramic wafers). The conductive strips typically comprise tungsten, gold, nickel, silver, platinum or equivalent materials. In the exemplary embodiment, the conductive strips comprise gold, and they are co-fired together with the wafer layers to form an integral package. The conductive strips are coupled to external wire connectors by holes or vias that are drilled through the ceramic layers, and plated or otherwise covered with conductive material.

In the representative embodiment, support member 70 comprises five ceramic layers 200, 202, 204, 206, 208 (see FIGS. 9-13), three gold plated electrode terminals 210, 212, 214 and first and second gold plated return electrodes 216, 218. As shown in FIGS. 8A, 9A and 9B, a first ceramic layer 200, which is one of the outer layers of support 70, includes first gold plated return electrode 216 on a lateral surface 220 thereof. First ceramic layer 200 further includes a gold conductive strip 222 extending from return electrode 216 to the proximal end of the layer 200 for coupling to a lead wire (not shown), and three gold conductive lines 224, 226, 228 extending from a mid-portion of the layer 200 to its proximal end. Conductive strips 224, 226, 228 are each coupled to one of the electrode terminals 210, 212, 214 by conductive holes or vias 230, 232, 234, respectively. As shown, all three vias 230, 232, 234 extend through wafer layer 200.

Figure 13:
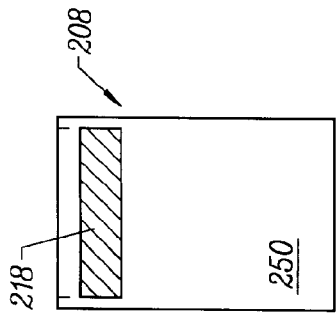
Figure 12A:
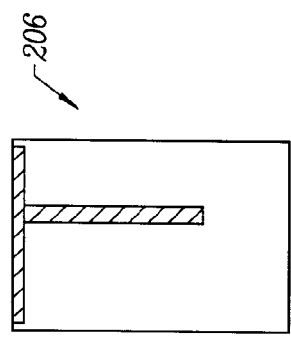
Figure 12B:
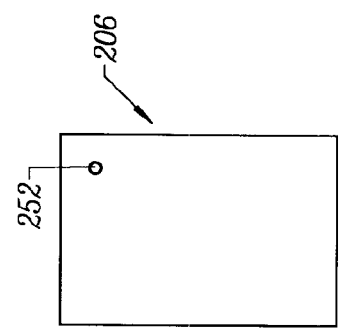
Figure 11A:
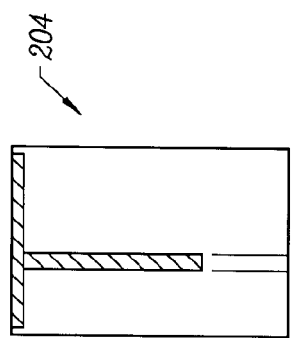
Figure 11B:
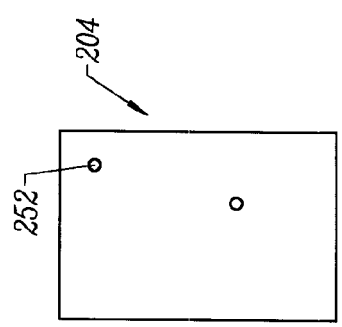

Referring to FIGS. 10A and 10B, a second wafer layer 202 is bonded between the outer wafer layer 200 and a middle wafer layer 204 (FIGS. 11A and 11B). As shown, first electrode terminal 210 is attached to the distal surface of second wafer layer 202, and a conductive strip 240 extends to via 230 to couple electrode terminal 210 to a lead wire. Similarly, wafer layers 204 and 206 (FIGS. 11 and 12) each have an electrode terminal 212, 214 plated to their distal surfaces, and a conductive strip 242, 244, respectively, extending to one of the vias 232, 234, respectively. Note that the vias only extend as far as necessary through the ceramic layers. As shown in FIG. 13, another outer wafer layer 208 has a second return electrode 218 plated to the lateral surface 250 of layer 208. The second return electrode 218 is coupled directly to the first return electrode 216 through a via 252 extending through the entire ceramic substrate.

Figure 14:
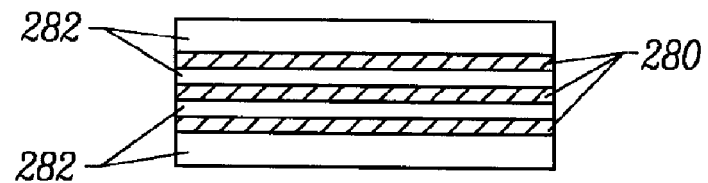
FIGS. 14 and 15 illustrate an alternative multi-layer wafer design according to the present invention.
Figure 15:
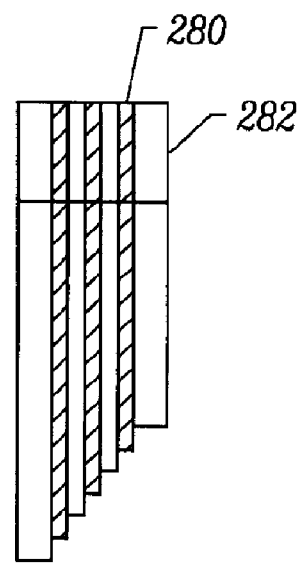

Of course, it will be recognized that a variety of different types of multilayer wafers may be constructed according to the present invention, For example, FIGS. 14 and 15 illustrate an alternative embodiment of the multilayer ceramic wafer, wherein the electrode terminals comprise planar strips 280 that are plated or otherwise bonded between the ceramic wafer layers 282. Each of the planar strips 280 has a different length, as shown in FIG. 15, so that the electrode terminals can be electrically isolated from each other, and coupled to lead wires by vias (not shown).

In another embodiment, the active electrode(s) are spaced from the tissue a sufficient distance to minimize or avoid contact between the tissue and the vapor layer formed around the active electrodes. In these embodiments, the amount of thermal energy delivered to the tissue is reduced by this spacing. In some embodiments, contact between the heated electrons in the vapor layer and the tissue is minimized as these electrons travel from the vapor layer back through the conductive fluid to the return electrode. The ions within the plasma, however, will have sufficient energy, under certain conditions such as higher voltage levels, to accelerate beyond the vapor layer to the tissue. Thus, the tissue bonds are dissociated or broken as in previous embodiments, while minimizing the electron flow, and thus the thermal energy, in contact with the tissue.

Figure 16:
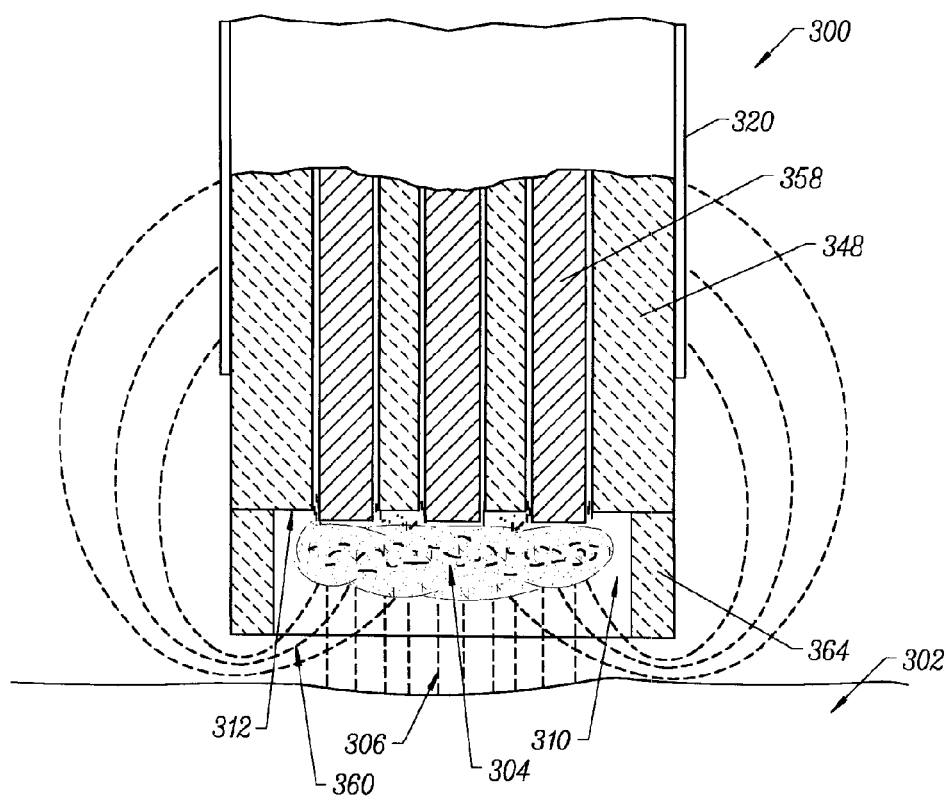
FIG. 16 illustrates the working end of an alternative electrosurgical probe incorporating an isolation shield according to the present invention.

FIG. 16 illustrates the working end of an electrosurgical probe 300 having a plurality of active electrode terminals 358 recessed from a distal surface 360 of an insulating support member 348 to prevent contact between electrode terminals 358 and the tissue 302. Preferably, electrode terminals 358 will be spaced a sufficient distance to prevent direct contact between the vapor layer 304 formed around terminals 358 and the tissue 302, while allowing ions 306 from the vapor layer 304 to reach the tissue 302 for the ablation process described above. This distance will vary with the voltage applied, the electrode configurations, the ionic concentration of the conductive fluid and other factors. In the representative embodiment, the electrode terminals 358 are spaced a distance of about 0.5 mm to 5.0 mm, preferably about 1.0 to 2.0 mm, from distal surface 360, and the applied voltage is about 200 to 300 volts rms or about 400 to 600 volts peak to peak (with a square waveform). In this embodiment, the conductive fluid is isotonic saline, which has a sodium chloride concentration of about 0.9%. Applicant has found that increasing the concentration of sodium chloride or increasing the voltage applied between the electrode terminals and the return electrode will increase the concentration and energy level of the ions within the plasma. Thus, the distance between the electrode terminals and the tissue can be increased which will, in some cases, reduce the temperature at the tissue surface.

As shown in FIG. 16, support member 348 includes an annular extension 364 that extends distally from the electrode terminals 358 and the inner portion 312 of support member 348. Annular extension 364 will preferably comprise an electrically insulating material, such as a ceramic or glass composition, or silicone, and it may comprise a transparent material that allows the physician to view the plasma chamber 310 formed therein. In the representative embodiment, the electrode terminals 358 extend distally from the inner portion 312 of support member 348. This configuration increases the current densities near the edges of electrode terminals 348 to increase the strength of the plasma 304 and the rate of ablation while still maintaining a space between the electrode terminals 348 and the distal surface 360 of annular extension 364. In this embodiment, a return electrode 320 is positioned proximally of electrode terminals 358, and outside of plasma chamber 310. However, the return electrode 320 may also be positioned within plasma chamber 310 if it is desired to confine the electric current to the plasma chamber 310 (see FIGS. 17 and 18). In this latter configuration, the return and active electrodes will be suitable configured and spaced to avoid current shorting therebetween.

In the representative embodiment, probe 300 is used in a wet field, or one that is already immersed in conductive fluid. However, it will be recognized that this embodiment may also be used in a dry field, wherein the conductive fluid is supplied to the target site, e.g., via a fluid lumen or tube within the probe. Preferably, the fluid tube(s) will have distal opening(s) within the plasma chamber 310 to allow for continual resupply of conductive fluid around electrode terminals 358 even if the surgeon presses the probe against the tissue, which reduces collateral damage to the tissue. In another embodiment (not shown), the probe will include an aspiration lumen (not shown) having a distal opening with the plasma chamber 310 such that excess fluid within the cavity is immediately aspirated through the lumen. This configuration, together with a return electrode positioned within the plasma chamber 310, allows the physician to create a closed fluid and electric circuit that minimizes fluid and current leakage outside of the plasma chamber 310.

In another embodiment, a screen made of a suitable material that will allow passage of vapor or the plasma layer while substantially preventing passage of fluid, such as a synthetic mesh material, closes the distal opening of the plasma chamber, minimizing the amount of fluid leaking out of the chamber, without significantly restraining the plasma field.

In the exemplary embodiment, the high frequency voltage applied between electrode terminals 358 and return electrode 320 is sufficient to convert the electrically conductive fluid between the target tissue and electrode terminals 358 into an ionized vapor layer or plasma 304, as discussed above. As a result of the applied voltage difference between electrode terminals 358 and the target tissue (i.e., the voltage gradient across the plasma layer 304), charged particles 306 in the plasma 304 (viz., electrons) are accelerated towards the tissue 302. At sufficiently high voltage differences, these charged particles 306 gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. The short range of the accelerated charged particles 306 within the target tissue 302 confines the molecular dissociation process to the surface layer to minimize damage and necrosis to the underlying tissue.

In some embodiments, the voltage difference will be sufficient enough to apply thermal energy to the underlying tissue. Preferably, this thermal energy will be sufficient to elevate the tissue temperature from normal body temperatures (e.g., 37° C.) to temperatures in the range of 45° C. to 90° C., preferably in the range from 55° C. to 70° C. and, for the case of skin, preferably in the range of about 55° C. to 62° C. This temperature elevation causes sufficient damage to the collagen connective fibers to enhance or stimulate regrowth of new collagen fibers in the underlying tissue.

Figure 17:
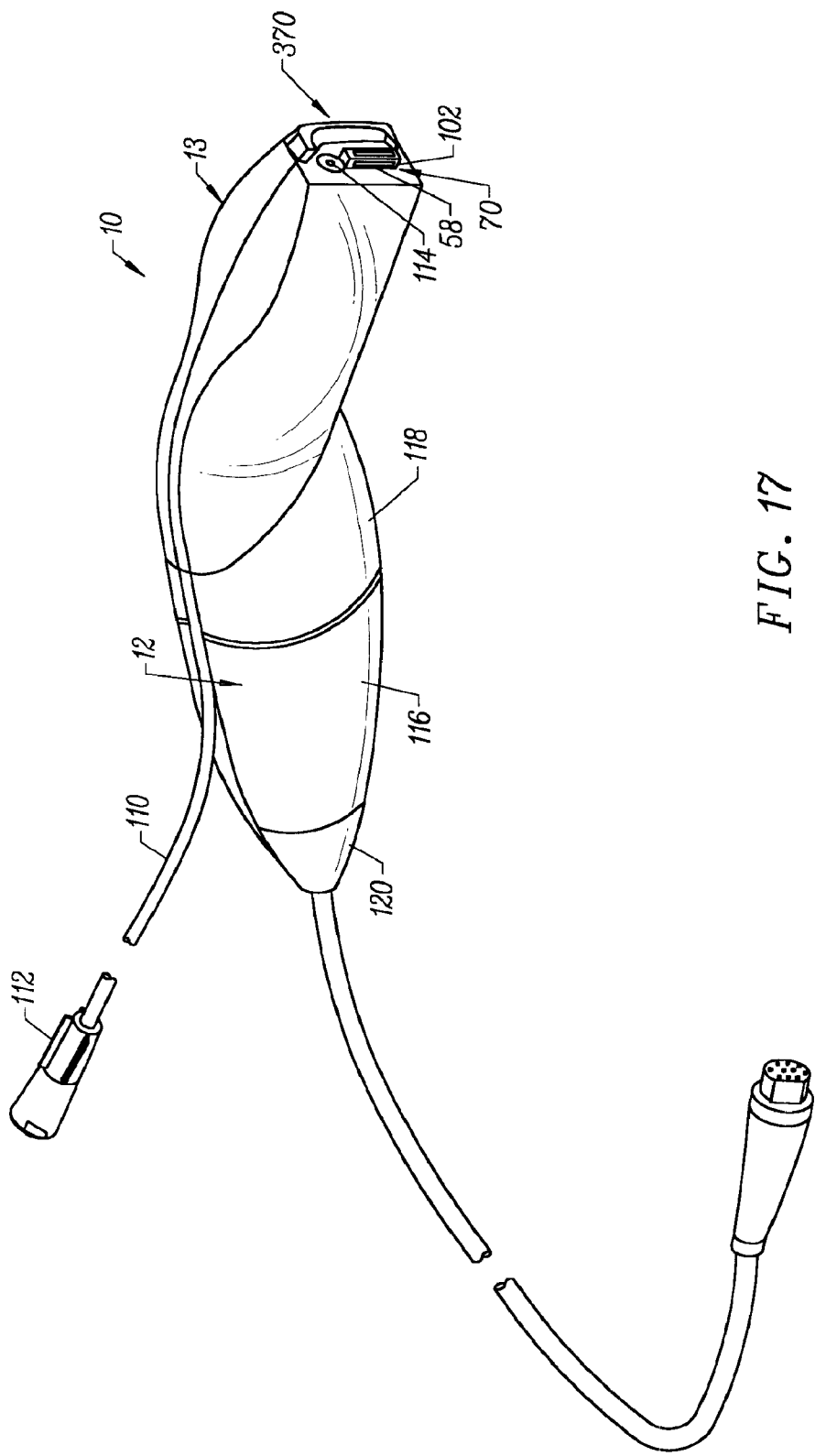
FIGS. 17 and 18 are two alternative embodiments of electrosurgical probes incorporating isolation shields.

FIG. 17 illustrates another embodiment of the present invention incorporating an isolation shield 370 that surrounds the electrode support member 70, including both the active electrodes 58 and the return electrodes 102, and the distal opening 114 of fluid tube 110. Note that only part of isolation shield 370 is shown in FIG. 17 to illustrate support member 70 and fluid tube opening 114. Isolation shield 370 preferably comprises an electrically insulating material, such as ceramic, silicone, glass or the like. Shield 370 is attached to the distal face of disposable tip 13 such that the entire working end (i.e., electrodes 58, 102 and fluid delivery opening 114) is surrounding by the shield. Shield 370 preferably extends about 0.2 to 3.0, typically about 0.5 to 1.5 mm from the distal end of active electrodes 58 to provide an offset between active electrodes 58 and the tissue. In this embodiment, the main difference is that the return electrodes 102 and the fluid delivery opening 114 are also housed within the plasma chamber created by shield 370. In the exemplary embodiment, isolation shield 370 comprises a transparent material, such as glass or plastic, such that the physician can see when the device is activated and the plasma field is being created around active electrodes 58 (typically indicated by an orange glow when isotonic saline is the conductive fluid).

Figure 18:
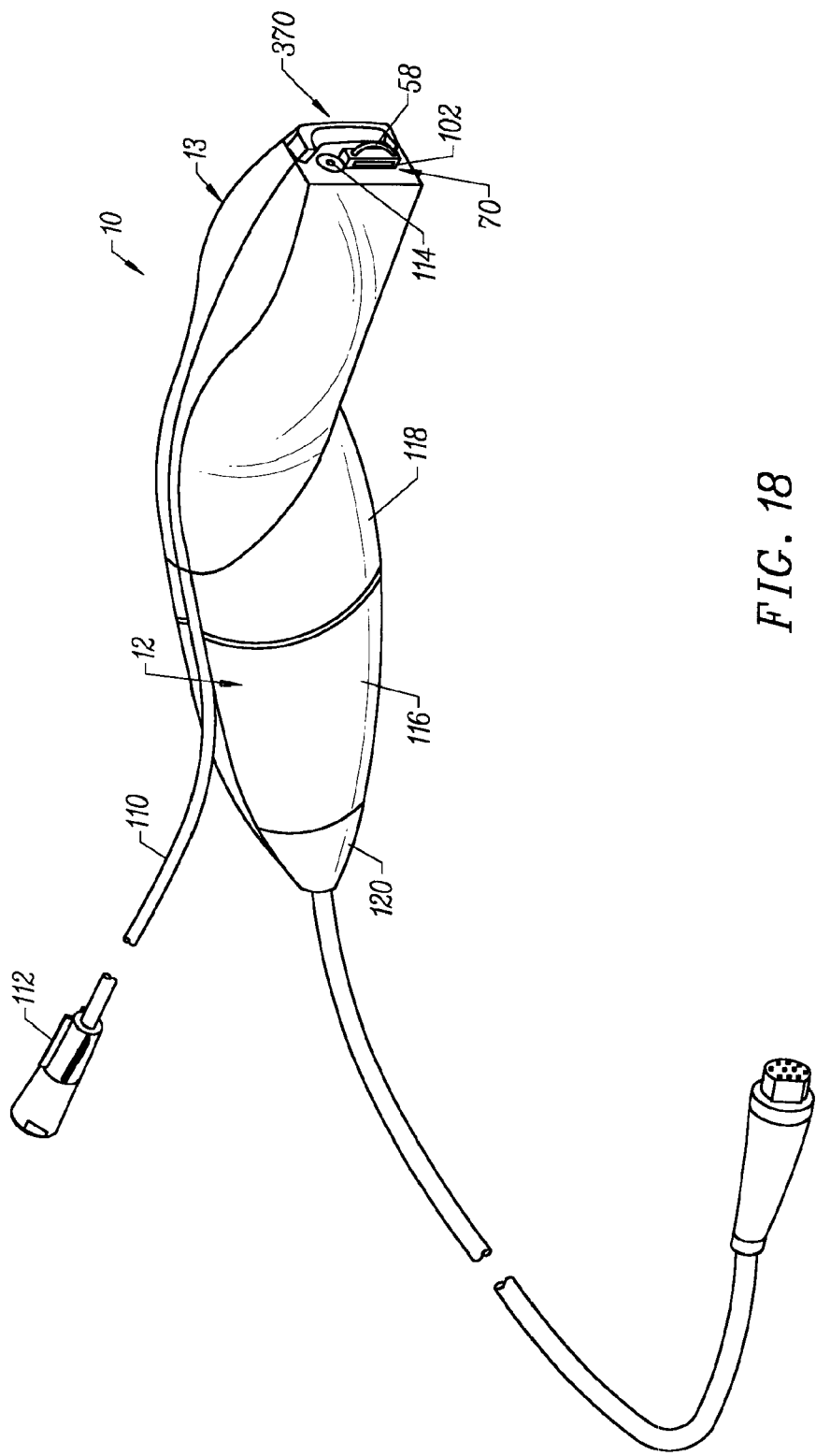

Referring now to FIG. 18, another embodiment of the present invention incorporating a loop electrode 58 to function as the active electrode. Applicant has found that the loop electrode 58 generally induces higher current densities than the flush electrode design shown in FIG. 17, which increases the electric fields around electrode 58, thereby increasing the strength of the plasma layer. This configuration allows the active loop electrode 58 to be held at a further distance away from the tissue (i.e., typically about 1.0-2.0 mm), while still maintaining sufficiently high electric fields to ablate the tissue. Spacing the loop electrode 58 further away from the tissue further minimizes current flow into the tissue and further reduces the temperature of the tissue (e.g., typically maintaining a tissue surface temperature less than about 50° C., often less than about 40° C.). In some applications, this enables the physician to remove the outer tissue layer (e.g., the stratum corneum) without applying anesthesia to the patient because the tissue temperature is below the threshold that would cause pain to the patient.

Figure 19:
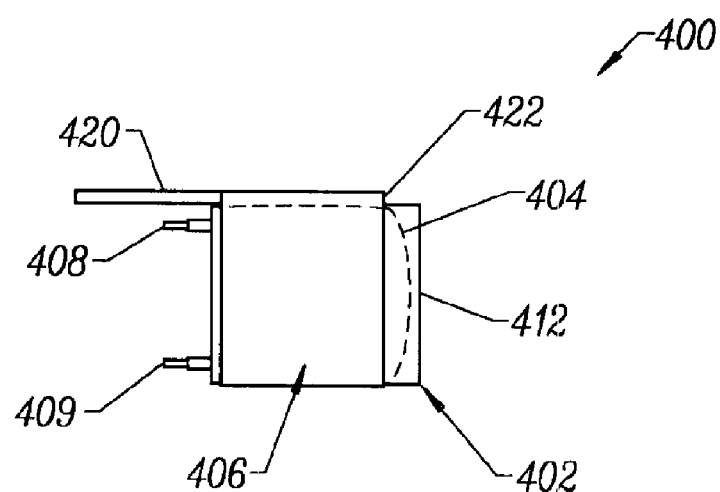
FIG. 19 illustrates a disposable tip for use with an electrosurgical probe, such as those shown in FIGS. 17 and 18.

FIG. 19 illustrates a disposable tip 400 for use with an electrosurgical probe similar to those shown in FIGS. 17 and 18. Tip 400 is designed to be attached and detached from a reposable handle (not shown) of the electrosurgical probe. In this embodiment, tip 400 comprises an electrically insulating support member 404 made from a material that may be molded over an active electrode 404 such that a thin, slit opening 412 is present at the distal surface of support member 402. As shown, the active electrode 404 comprises a loop electrode 404 as in the embodiment of FIG. 18. Slit opening 412 allows electrically conductive fluid to be delivered within support member 402 to active electrode 404 such that electric current can travel through the conductive fluid to a return electrode 406 surrounding the support member 404. As shown, return electrode 406 is proximally spaced from the distal portion of active electrode 404 and opening 412 to avoid contact between return electrode 406 and the tissue. Electrical connectors 408, 410 are coupled to active and return electrodes 402, 406, respectively, for electrically coupling tip 400 to a handle (not shown) of an electrosurgical probe (not shown).

The support member 404 preferably comprises an inorganic material similar to other embodiments. Applicant has found that a silicone material effectively insulates the active electrode 404 from the return electrode 406, and can be molded using liquid injection molding or similar techniques. In addition, a silicone material will tend to resist the plasma layer formed around active electrode 404. Support member 404 is also designed to fluidly seal the interior of the handle (not shown) after tip 400 is coupled to handle to prevent fluid ingress into the handle of the probe. Alternatively, a separate seal (not shown), such as an O-ring or similar device, may be used to enhance the seal between the tip 400 and the handle.

As shown, tip 400 further includes a fluid tube 420 that extends through tip 400 to an opening 422 at the distal end of return electrode 406. Fluid tip 420 is adapted for coupling to a fluid tube or lumen (not shown) in the handle to deliver electrically conductive fluid to the target site. As discussed in detail above, tip 400 may be used within a conductive gel or another material that is applied directly to the target site or to tip 400. In these embodiments, the fluid tube 420 may not be required.

Figure 20:
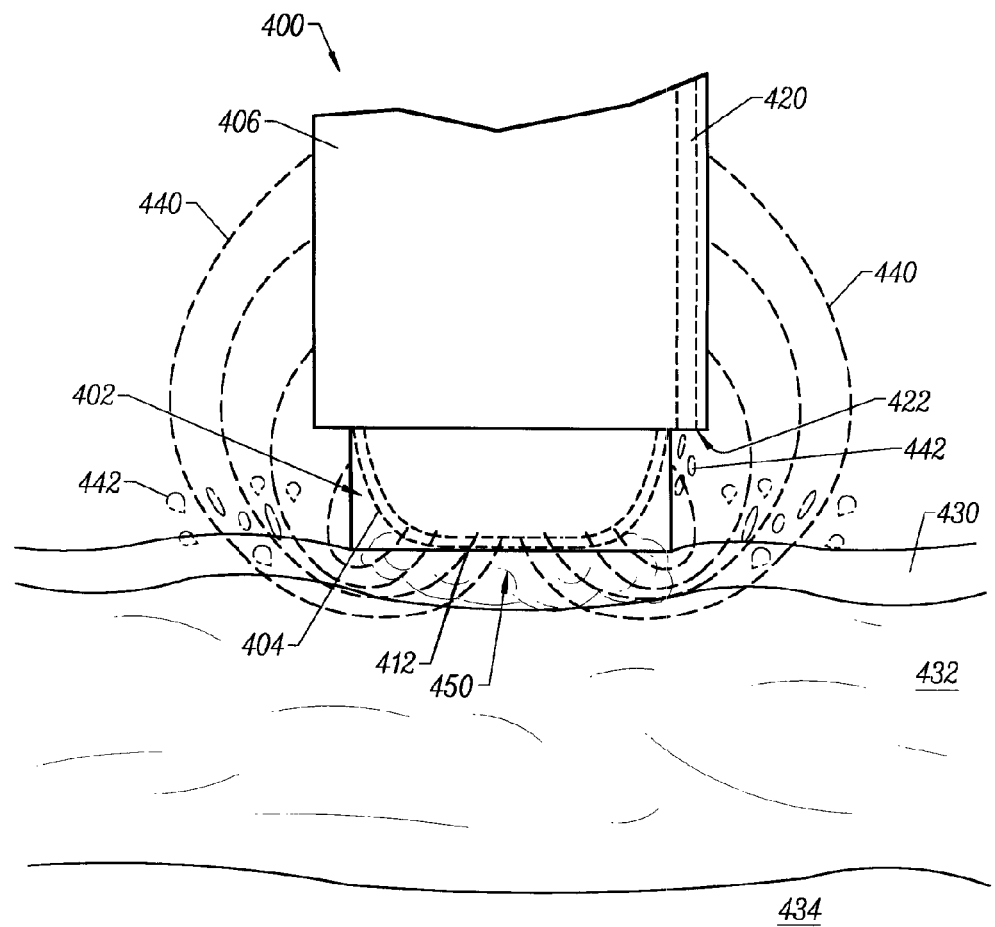
FIGS. 20 and 21 illustrate methods for removing the stratum corneum according to the present invention.

FIG. 20 illustrates a method for removing the stratum corneum 430, i.e., the top superficial layer of dead skin cells, of a patient without entirely removing or permanently damaging the underlying epidermis layer 432. As shown, a tip 400 of an electrosurgical probe (not shown) is positioned adjacent the target site such that active loop electrode 404 is spaced a distance of about 0.2 to 2.0 mm from the stratum corneum 430. This can be accomplished by pressing the distal surface of the electrode support member 402 against the stratum corneum 430 or bring this distal surface extremely close to the surface of the stratum corneum 430. Electrically conductive fluid 442, such as isotonic saline, is delivered through tube 420 to the target site such that a conductive path is formed through the fluid 442 between active and return electrodes 402, 406. In addition, a sufficient quantity of conductive fluid is present around active electrode 402 to form a vapor layer 450 within or around support member 402 as discussed in detail above.

FIG. 20 illustrates the current flux lines 440 associated with an electric field applied between the active and return electrodes 404, 406 when a voltage is applied therebetween. The electric field intensity is substantially higher in the region near loop electrode 404 because the current flux lines are concentrated in these regions. In one embodiment, this high electric field intensity leads to induced molecular breakdown of the target stratum corneum tissue 430 through molecular dissociation. As a result of the applied voltage difference between electrode terminal(s) 404 and the target tissue 430 (i.e., the voltage gradient across the plasma layer 450), charged particles (not shown) in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases (not shown), such as oxygen, nitrogen, carbon dioxide, hydrogen and methane. The short range of the accelerated charged particles within the tissue confines the molecular dissociation process to the surface layer to minimize damage and necrosis to the underlying tissue.

Figure 21:
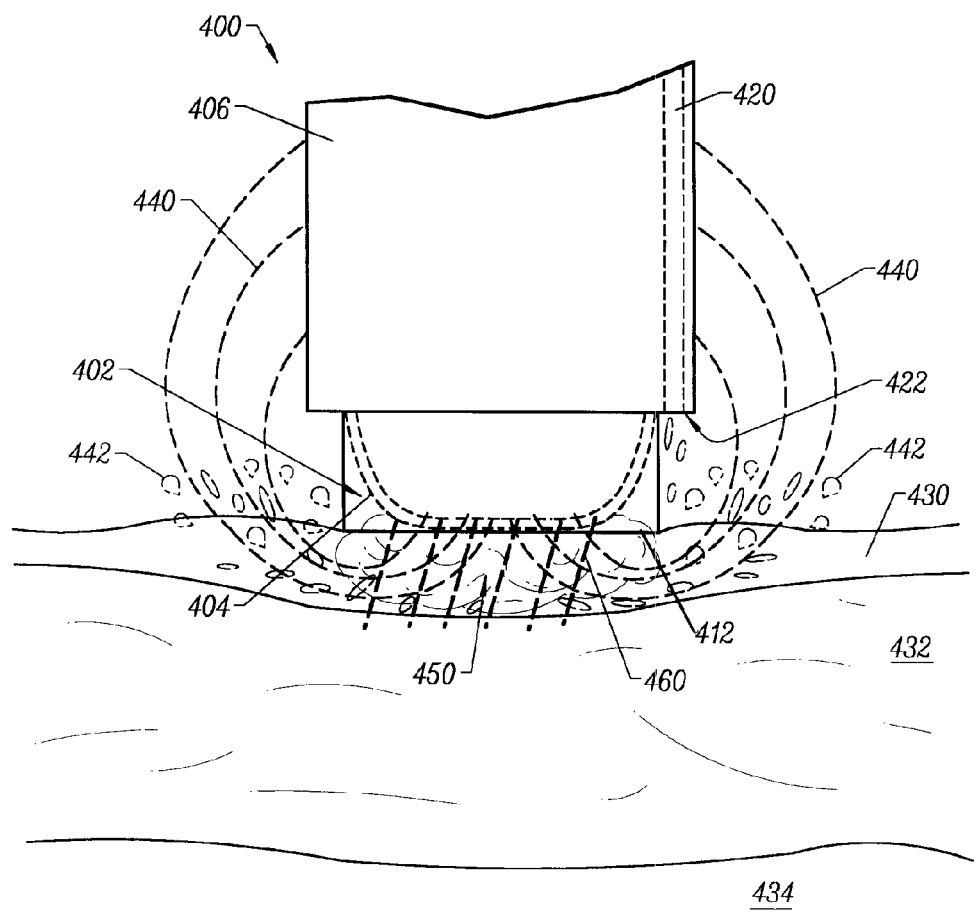

Referring to FIG. 21, in one embodiment, active loop electrode 404 will be spaced a sufficient distance from tissue surface 430 to prevent direct contact between the vapor layer 450 formed around electrode 404 and the tissue 430, while allowing ions 460 from the vapor layer 450 to reach the tissue 430 for the ablation process described above. This distance will vary with the voltage applied, the electrode configurations, the ionic concentration of the conductive fluid and other factors. In the representative embodiment, the loop electrode is spaced a distance of about 1.0 mm to 5.0 mm, preferably about 2.0 mm, from the distal surface 412 of support member 402, and the applied voltage is about 150 to 350 volts rms or about 300 to 700 volts peak to peak (with a square waveform), typically about 200 to 300 volts rms or 400 to 600 volts peak to peak. Alternative, the loop electrode 404 may be spaced closed to the distal surface 412 of support member 404, and the physician may be instructed to maintain a space between distal surface 412 and the tissue 430 during the procedure.

For particular applications, it may be desirable to further reduce the tissue temperature by maintaining relatively low plasma temperatures, e.g., below 100° C., below 80° C., or even below 50° C. This low temperature tissue removal reduces the likelihood of collateral thermal damage to those cells or tissue surrounding the target tissue, and reduces the need for anesthesia during the procedure.

With a lowered vaporization temperature, the energy levels sufficient for ablation of tissue can be reached while decreasing the thermal energy directed to the tissue. One technique for achieving the desired decrease in temperature of volumetric tissue removal is to use an electrically conductive liquid having a vaporization temperature below 100° C., or below 80° C. Applicant believes that the temperature of vaporization into a ionized plasma according to the methods of the present invention is related to the boiling temperature of the liquid. Boiling temperature of a liquid is defined as the temperature of a liquid at which its vapor pressure is equal to or very slightly greater than the atmospheric or external pressure of the environment. As is well known, the boiling temperature of water at sea level (1 atms) is 100° C.

A variety of fluids and/or solutions have boiling temperatures below 100° C. For example, methanol has a boiling temperature of 64.7° C. Preferably, the fluid or solution will comprise an electrically conductive, biocompatible material that is not toxic or harmful to the patient. In addition, for some applications such as arthroscopy, it is further desirable to minimize absorption of the conductive solution into the surrounding tissue cells. It may further be desirable that the liquid solution be an azeotropic. Azeotropic mixtures of two or more substances behave like a single substance in that the vapor produced by partial evaporation of liquid has the same composition as the liquid. This should prevent the uneven depletion of one solution component faster than the other, which may over the course of treatment, undesirably change the boiling temperature.

Another technique for lowering the vaporization temperature of the electrically conductive fluid involves reducing the external vapor pressure of the air or gas near the target site. The boiling temperature of water decreases with pressure. Thus, by creating a sub-atmospheric environment in the electrically conductive fluid near the electrode terminal(s), the temperature required for vaporization of the fluid will decrease.

In another embodiment, the electrically conductive fluid, typically isotonic saline, is cooled prior to its delivery to the target site. Typically, the conductive fluid will be cooled to a temperature in the range of about 0° C. to 20° C., usually about 5° C. to 15° C. In addition, the probe may incorporate suction near the tip 400 so that the conductive fluid is withdrawn from the target site after it has accomplished the function of providing a conductive path between the active and return electrodes and forming a vapor layer around the active electrode. These features accomplish two functions: (1) the conductive fluid that reaches the target site is cooler, which further reduces the tissue temperature; (2) as the electric fields increase the temperature of the conductive fluid around the active electrode, this hotter conductive fluid is aspirated from the target site; and (3) a convective cooling process is established by the cool fluid that moves through the target site and back through the aspiration lumen.

Applicant has found that increasing the current densities around the electrode terminal(s) can lead to higher energy levels in the ionized plasma at the same or similar temperatures. This, in turn, allows the ionized plasma to break stronger molecular bonds, such as those present in bone or calcified fragments, or to ablate tissue at further distances away from the tissue. Since the electrically conductive fluid between the target site and electrode terminal(s) is transformed into an ionized vapor layer or plasma, the number of charged particles which can be accelerated against the target also determines the removal rate. In addition, the conductivity of the fluid may have an effect on the strength of the plasma field created at the end of the probe. Typically, isotonic saline with 0.9% concentration of sodium chloride is used with the probe. By increasing the sodium chloride concentration to greater than 0.9% and preferably between about 3% and 20%, the increased concentration provides for improved tissue ablation rates.

Applicant has also found that the plasma layer typically requires a higher voltage level to initiate a plasma than to sustain the plasma once it has been initiated. In addition, it has been found that some conductive solutions facilitate the initiation of the plasma layer, rather than the energy level of the plasma, as discussed above. For example, it has been found that saline solutions having concentrations less than isotonic saline (i.e., less than 0.9% sodium chloride) facilitate the initiation of the plasma layer. This may be useful in applications where initiation of the plasma layer is more difficult, such as applications where a suction pressure is applied near the electrode terminal(s). A more complete description of this type of application, and the devices that carry out simultaneous suction and ablation can be found in U.S. patent application Ser. No. 09/010,382, filed Jan. 21, 1998, the complete disclosure of which is incorporated herein by reference for all purposes.

What is claimed is:

1. A method for applying electrical energy to a patient's outer skin comprising:
   positioning an active electrode adjacent to or near a target site on a patient's outer skin; and
   applying sufficient high frequency voltage to the active electrode to volumetrically remove a substantially continuous layer of the stratum corneum adjacent to or near the target site in order to improve the surface appearance of the patient's outer skin without removing the entire epidermis layer.

2. The method of claim 1 further comprising removing a layer of skin having a thickness less than about 30 microns.

3. The method of claim 1 further comprising stimulating the growth of new collagen in the patient's skin underlying the removed stratum corneum.

4. The method of claim 3 wherein the stimulating step is carried out by removing the dead skin cells from the patient's outer skin and accelerating the growth of new skin cells.

5. The method of claim 3 wherein the stimulating step is carried out by applying thermal energy to the underlying dermis and epidermis.

6. The method of claim 1 further comprising applying a high frequency voltage difference between the active electrode and a return electrode in the presence of an electrically conductive fluid, wherein the conductive fluid generates a conductive path between the active and return electrodes.

7. The method of claim 6 further comprising applying a sufficient high frequency voltage difference between the active and return electrodes to vaporize a portion of the electrically conductive fluid, and to ionize the vaporized fluid into a plasma adjacent to the active electrode.

8. The method of claim 6 further comprising delivering the electrically conductive fluid to the target site during the applying step.

9. The method of claim 8 further comprising cooling the electrically conductive fluid.

10. The method of claim 1 further comprising maintaining a space between the active electrode and the patient's outer skin during the applying step.

11. The method of claim 10 wherein the space is at least about 0.5 mm.

12. The method of claim 10 wherein the space is at least about 1.0 mm.

13. A method for applying electrical energy to a patient's outer skin comprising:
   positioning an active electrode adjacent to or near a target site on a patient's outer skin having a first outer layer and a second layer underlying the first outer layer; and
   applying sufficient high frequency voltage to the active electrode to volumetrically remove a substantially continuous portion of the first outer layer adjacent to or near the target site in order to improve the surface appearance of the patient's outer skin while maintaining a temperature at the exposed surface of the second layer less than about 50° C.

14. The method of claim 13 wherein the temperature at the exposed surface of the second layer is less than about 40° C.

15. The method of claim 13 wherein the first layer has a thickness in the range of about 5 to 30 microns.

16. The method of claim 13 wherein the first layer is the stratum corneum and the second layer is the epidermis.

17. The method of claim 13 further comprising stimulating the growth of new collagen in the patient's skin underlying the first outer layer.

18. The method of claim 13 further comprising applying a high frequency voltage difference between the active electrode and a return electrode in the presence of an electrically conductive fluid, wherein the conductive fluid generates a conductive path between the active and return electrodes.

19. The method of claim 18 further comprising applying a sufficient high frequency voltage difference between the active and return electrodes to vaporize a portion of the electrically conductive fluid, and to ionize the vaporized fluid into a plasma adjacent to the active electrode.

20. The method of claim 18 further comprising delivering the electrically conductive fluid to the target site during the applying step.

21. The method of claim 20 further comprising cooling the electrically conductive fluid prior to the delivering step.

22. The method of claim 13 further comprising maintaining a space between the active electrode and the first outer layer during the applying step.

23. The method of claim 22 wherein the space is at least about 1.0 mm.

* * * * *